US008680059B2

(12) United States Patent
Khan et al.

(10) Patent No.: US 8,680,059 B2
(45) Date of Patent: *Mar. 25, 2014

(54) OLIGOPEPTIDE ACETATE AND FORMULATIONS THEREOF

(75) Inventors: Nisar Ahmed Khan, Rotterdam (NL); Robbert Benner, Barendrecht (NL)

(73) Assignee: Biotempt B.V., Koekange (NL)

( * ) Notice: Subject to any disclaimer, the term of this patent is extended or adjusted under 35 U.S.C. 154(b) by 1248 days.

This patent is subject to a terminal disclaimer.

(21) Appl. No.: 11/600,294

(22) Filed: Nov. 15, 2006

(65) Prior Publication Data
US 2007/0197447 A1 Aug. 23, 2007

Related U.S. Application Data

(63) Continuation-in-part of application No. 10/409,668, filed on Apr. 8, 2003, now abandoned, and a continuation-in-part of application No. 11/037,972, filed on Jan. 18, 2005, now Pat. No. 7,820,617, which is a continuation of application No. 09/821,380, filed on Mar. 29, 2001, now Pat. No. 6,844,315, which is a continuation-in-part of application No. 09/716,777, filed on Nov. 20, 2000, now Pat. No. 6,921,751, which is a continuation of application No. PCT/NL99/00313, filed on May 20, 1999, application No. 11/600,294, which is a continuation-in-part of application No. 10/262,522, filed on Sep. 30, 2002, now Pat. No. 7,365,155, which is a continuation of application No. PCT/NL01/00259, filed on Mar. 3, 2001.

(30) Foreign Application Priority Data

May 20, 1998 (EP) .................................... 98201695
Aug. 12, 1998 (EP) .................................... 98202706
Mar. 29, 2000 (EP) .................................... 00201139

(51) Int. Cl.
*A61K 38/06* (2006.01)
*C09D 101/14* (2006.01)

(52) U.S. Cl.
USPC ........................................... 514/21.9; 524/39

(58) Field of Classification Search
None
See application file for complete search history.

(56) References Cited

U.S. PATENT DOCUMENTS

| | | | |
|---|---|---|---|
| 4,330,466 A | 5/1982 | Yanaihara et al. | |
| 4,427,660 A | 1/1984 | Schiffman et al. | |
| 4,571,336 A | 2/1986 | Houck et al. | |
| 4,753,965 A | 6/1988 | Stemerick et al. | |
| 4,855,285 A | 8/1989 | Stevens | |
| 4,966,848 A * | 10/1990 | Smith et al. | 435/193 |
| 4,977,244 A | 12/1990 | Muchmore et al. | |
| 5,002,961 A | 3/1991 | Dage et al. | |
| 5,010,175 A | 4/1991 | Rutter et al. | |
| 5,055,447 A | 10/1991 | Palladino et al. | |
| 5,102,393 A | 4/1992 | Sarnoff et al. | |
| 5,223,397 A | 6/1993 | Pouletty | |
| 5,223,421 A * | 6/1993 | Smith et al. | 435/193 |
| 5,308,834 A | 5/1994 | Scott et al. | |
| 5,380,668 A | 1/1995 | Herron | |
| 5,436,270 A | 7/1995 | Wang | |
| 5,677,275 A | 10/1997 | Lunardi-Iskandar et al. | |
| 5,700,781 A | 12/1997 | Harris | |
| 5,801,193 A | 9/1998 | Ojo-Amaize et al. | |
| 5,837,218 A * | 11/1998 | Peers et al. | 424/1.69 |
| 5,837,478 A | 11/1998 | Gallatin et al. | |
| 5,851,997 A | 12/1998 | Harris | |
| 5,854,004 A | 12/1998 | Czernilofsky et al. | |
| 5,856,440 A | 1/1999 | Wang | |
| 5,877,148 A | 3/1999 | Lunardi-Iskandar et al. | |
| 5,942,494 A | 8/1999 | Ginsberg et al. | |
| 5,958,413 A | 9/1999 | Anagnostopulos et al. | |
| 5,966,712 A | 10/1999 | Sabatini et al. | |
| 5,968,513 A | 10/1999 | Gallo et al. | |
| 5,972,924 A | 10/1999 | Keep et al. | |
| 5,981,486 A | 11/1999 | Matsushima et al. | |
| 5,994,126 A | 11/1999 | Steinman et al. | |
| 5,997,871 A | 12/1999 | Gallo et al. | |
| 6,022,696 A | 2/2000 | Harding et al. | |
| 6,051,596 A | 4/2000 | Badger | |
| 6,075,150 A | 6/2000 | Wang et al. | |
| 6,086,918 A | 7/2000 | Stern et al. | |
| 6,150,500 A | 11/2000 | Salerno | |
| 6,207,145 B1 | 3/2001 | Tovey | |
| 6,235,281 B1 | 5/2001 | Stenzel et al. | |
| 6,271,199 B2 | 8/2001 | Brand et al. | |
| 6,278,794 B1 | 8/2001 | Parekh et al. | |
| 6,309,822 B1 | 10/2001 | Fodor et al. | |

(Continued)

FOREIGN PATENT DOCUMENTS

EP 0 572 688 5/1997
EP 1 138 692 A1 10/2001

(Continued)

OTHER PUBLICATIONS

R.J. Bastin, et al. Org. Proc. Res. Develop. (2000) 4, pp. 427-435.*
P.L. Gould. Int. J. Pharm. (1986) 33, pp. 201-217.*
Retrieved from Website: http://www.ncbi.nlm.nih.gov/pubmed/1150658, 9 pages, retrieved on Mar. 23, 2013.*
Audran, M., Iatrogenic Demineralizing osteopathies, Presse Med. Feb. 12, 1994: 23(6); 271-3.
Bardin, et al., Nephrogenic systemic fibrosis, Current Opinion in Rheumatology 2010, 22:54-58.
Chiao, et al., α-Melanocyte-stimulating Hormone Protects Against Renal Injury after Ischemia in Mice and Rats. The American Society for Clinical Investigation. Inc., vol. 99, No. 6: Mar. 1997, 1165-1172.

(Continued)

Primary Examiner — Satyanarayana R Gudibande
(74) Attorney, Agent, or Firm — TraskBritt, P.C.

(57) ABSTRACT

The invention relates to acetates of the tetrapeptides AQGV (SEQ ID NO:2) and LQGV (SEQ ID NO:3), pharmaceutical compositions comprising the acetates of the tetrapeptides, and methods of treating using the acetates of the tetrapeptides or pharmaceutical compositions to treat acute inflammatory conditions including sepsis.

6 Claims, 3 Drawing Sheets

(56) References Cited

U.S. PATENT DOCUMENTS

| | | |
|---|---|---|
| 6,310,041 B1 | 10/2001 | Haddox et al. |
| 6,319,504 B1 | 11/2001 | Gallo et al. |
| 6,329,573 B1 | 12/2001 | Lightfoot et al. |
| 6,361,992 B1 | 3/2002 | Szkudlinski et al. |
| 6,379,970 B1 | 4/2002 | Liebler et al. |
| 6,416,959 B1 | 7/2002 | Giuliano et al. |
| 6,489,296 B1 | 12/2002 | Grinnell et al. |
| 6,507,788 B1 | 1/2003 | Camara y Ferrer et al. |
| 6,518,021 B1 | 2/2003 | Thastrup et al. |
| 6,539,102 B1 | 3/2003 | Anderson et al. |
| 6,583,109 B1 | 6/2003 | Gallo et al. |
| 6,586,403 B1 | 7/2003 | Mathison et al. |
| 6,596,688 B1 | 7/2003 | Gallo et al. |
| 6,620,416 B1 | 9/2003 | Gallo et al. |
| 6,630,138 B2 | 10/2003 | Gerlitz et al. |
| 6,642,201 B1 | 11/2003 | Khavinson et al. |
| 6,645,934 B1 | 11/2003 | Rodemann et al. |
| 6,652,860 B1 | 11/2003 | Singh et al. |
| 6,699,656 B2 | 3/2004 | Gallo et al. |
| 6,711,563 B1 | 3/2004 | Koskas |
| 6,727,227 B1 | 4/2004 | Khavinson |
| 6,783,757 B2 | 8/2004 | Brudnak |
| 6,831,057 B2 | 12/2004 | Baldwin et al. |
| 6,844,315 B2 * | 1/2005 | Khan et al. .......... 514/1.4 |
| 6,852,697 B1 | 2/2005 | Mathison et al. |
| 6,894,028 B2 | 5/2005 | Lipton et al. |
| 6,921,751 B1 | 7/2005 | Khan et al. |
| 7,094,760 B2 | 8/2006 | Mathison et al. |
| 7,135,286 B2 | 11/2006 | Margus et al. |
| 7,175,679 B2 * | 2/2007 | Khan et al. .......... 514/2 |
| 7,316,819 B2 | 1/2008 | Grotts et al. |
| 7,358,330 B2 | 4/2008 | Khan et al. |
| 7,365,155 B2 * | 4/2008 | Khan et al. .......... 530/330 |
| 7,368,535 B2 | 5/2008 | Gorczynski et al. |
| 7,402,322 B2 | 7/2008 | Khan et al. |
| 7,501,391 B2 | 3/2009 | Khan et al. |
| 7,517,529 B2 * | 4/2009 | Khan et al. .......... 424/198.1 |
| 7,560,433 B2 | 7/2009 | Khan et al. |
| 2002/0041871 A1 | 4/2002 | Brudnak |
| 2002/0064501 A1 | 5/2002 | Khan et al. |
| 2002/0147306 A1 | 10/2002 | Lin et al. |
| 2003/0049273 A1 | 3/2003 | Gallo et al. |
| 2003/0113733 A1 | 6/2003 | Khan et al. |
| 2003/0119720 A1 | 6/2003 | Khan et al. |
| 2003/0148955 A1 | 8/2003 | Pluenneke |
| 2003/0166556 A1 | 9/2003 | Khan et al. |
| 2003/0186244 A1 | 10/2003 | Margus et al. |
| 2003/0215434 A1 | 11/2003 | Khan et al. |
| 2003/0219425 A1 | 11/2003 | Khan et al. |
| 2003/0220257 A1 | 11/2003 | Benner et al. |
| 2003/0220258 A1 | 11/2003 | Benner et al. |
| 2003/0220259 A1 | 11/2003 | Benner et al. |
| 2003/0220260 A1 | 11/2003 | Khan et al. |
| 2003/0220261 A1 | 11/2003 | Khan et al. |
| 2003/0224995 A1 | 12/2003 | Khan et al. |
| 2004/0013661 A1 | 1/2004 | Wensvoort et al. |
| 2004/0208885 A1 | 10/2004 | Khan et al. |
| 2005/0037430 A1 | 2/2005 | Khan et al. |
| 2005/0107314 A1 | 5/2005 | Gorczynski et al. |
| 2005/0214943 A1 | 9/2005 | Khan et al. |
| 2005/0227925 A1 | 10/2005 | Benner et al. |
| 2006/0111292 A1 | 5/2006 | Khan et al. |
| 2006/0142205 A1 | 6/2006 | Benner et al. |
| 2006/0173162 A1 * | 8/2006 | Djurup et al. .......... 530/324 |
| 2006/0275255 A1 | 12/2006 | Gudkov |
| 2007/0111948 A1 | 5/2007 | Turdiev |
| 2007/0197447 A1 | 8/2007 | Khan et al. |
| 2008/0076714 A1 | 3/2008 | Khan et al. |
| 2008/0171094 A1 | 7/2008 | Benner et al. |
| 2008/0176243 A1 | 7/2008 | Khan et al. |
| 2008/0194489 A1 | 8/2008 | Khan et al. |
| 2008/0242618 A1 | 10/2008 | Khan et al. |
| 2008/0242837 A1 | 10/2008 | Khan et al. |

FOREIGN PATENT DOCUMENTS

| | | |
|---|---|---|
| EP | 1 300 418 | 4/2003 |
| EP | 1 224 212 B1 | 7/2003 |
| EP | 1 466 612 A1 | 10/2004 |
| GB | 2 194 886 A | 3/1988 |
| JP | 09-176187 A | 7/1997 |
| JP | 2003 516931 | 5/2003 |
| WO | WO 80/02459 | 11/1980 |
| WO | WO 92/20795 A1 | 11/1992 |
| WO | WO 96/04008 | 2/1996 |
| WO | WO 96/33218 | 10/1996 |
| WO | WO 97/49373 | 12/1997 |
| WO | WO 97/49418 | 12/1997 |
| WO | WO 97/49432 | 12/1997 |
| WO | WO 97/49721 | 12/1997 |
| WO | WO 98/06742 | 2/1998 |
| WO | WO 98/34631 A1 | 8/1998 |
| WO | WO 98/35691 | 8/1998 |
| WO | WO 99/31227 | 6/1999 |
| WO | WO 99/59617 | 11/1999 |
| WO | WO 00/17348 | 3/2000 |
| WO | WO 01/10907 A2 | 2/2001 |
| WO | WO 01/11048 A2 | 2/2001 |
| WO | WO 0110457 A2 | 2/2001 |
| WO | WO 01/29067 | 4/2001 |
| WO | WO 01/29069 A1 | 4/2001 |
| WO | WO 01/32196 A1 | 5/2001 |
| WO | WO 01/36454 A1 | 5/2001 |
| WO | WO 01/51508 A1 | 7/2001 |
| WO | WO 01/68113 A1 | 9/2001 |
| WO | WO 01/72831 | 10/2001 |
| WO | WO 01/83554 A2 | 11/2001 |
| WO | WO 02/085117 | 10/2002 |
| WO | WO 03/029292 | 4/2003 |
| WO | WO 03/029292 A2 | 4/2003 |
| WO | WO 2006/069198 A1 | 6/2006 |

OTHER PUBLICATIONS

Hunsinger, et al., Is therea basis for novel pharmacotherapy of autism?, Life Sciences 67 (2000) 1667-1682.

Invernizzi, et al., Osteoporosis in Parkinson's disease, Parkinsonism Relat Disord. Jun. 2009: 15(5); 339-46.

Jensen, et al., Xerostomia and hypofunction of the salivary glands in cancer therapy, Support Care Cancer (2003)11:207-225.

Kintzel, PE., Anticancer drug-induced kidney disorders, Drug Saf. Jan. 2001; 24(1): 19-38.

Lyons. II. et al., Diabetes Management: Current Diagnostic Criteria, Drug Therapies, and State Legislation: The American Journal of Managed Care vol. 3. No. 10; Oct. 1997: pp. 1599-1612.

Manna, et al., α-Melanocyte-Stimulating Hormone Inhibits the Nuclear Transcription Factor NF-κB Activation Induced by Various Inflammatory Agents, The American Association of Immunologists, 1998; pp. 2873-2880.

Toyooka, et al., Iatrogenic neuropathies, Current Opinion in Neurology 2009; 22:475-479.

Waldum, et al., Antiulcer Drugs and Gastric Cancer, Digestive Diseases and Sciences, vol. 50, Supplement I (Oct. 2005); pp. S39-S44.

Will, Robert G., Acquired prion disease: iatrogenic CJD. variant CJD, kuru, British Medical Bulletin 2003: 66: 255-265.

Barton et al., Protective Role of Interleukin 6 in the Lipopolysaccharide-Galactosamine Septic Shock Model. Infection and Immunity. Apr. 1993, pp. 1496-99, vol. 61, No. 4.

Baud et al., Signaling by proinflammatory cytokines: oligomerization of TRAF2 and TRAF6 is sufficient for JNK and IKK activation and target gene induction via an amino-terminal effector domain, Genes & Development, May 1999, pp. 1297-1308, vol. 13.

Borchardt, RT, Optimizing oral absorption of peptides using prodrug strategies, Journal of Controlled Release, Nov. 1999, pp. 231-238, vol. 62.

Burdelya et al., An agonist of toll-like receptor 5 has radioprotective activity in mouse and primate models, Abstract. Science, Apr. 11, 2008. pp. 226-230, vol. 320, No. 5873.

Burdelya et al., NF-kappaB activating proteins as radioprotectants: Derivatives of Flagellin from Salmonella protect mice from hematopoietic and gastrointestinal Radiation Syndromes, Cleveland Biolabs, Inc., 2004.

(56) References Cited

OTHER PUBLICATIONS

Capizzi, Investigational New Drugs, 1996, 14:249-256.
Clerici et al., Single-cell analysis of cytokine production shows different immune profiles in multiple sclerosis patients with active or quiescent disease. Journal of Neuroimmunology, vol. 121, pp. 33-101, 2001.
Cleveland BioLabs, Inc., Radiation Antidote for Defense, (visited Apr. 16, 2008) <http://www.cbiolabs.com/Applications.php.
Corvino et al., Availability, stability and sterility of pralidoxime for mass casualty use, Abstract, Ann Emerg Med., Mar. 2006. pp. 272-277. vol. 47, No. 3.
Daemen et al., Ischemia-reperfusion-induced IFN-gamma up-regulation: involvement of IL-12 and IL-13. The Journal of Immunology. 1999, pp. 5506-5510, vol. 162.
Dietrich et al., Postischemic hypothermia and IL-10 treatment provide long-lasting neuroprotection of CAI hippocampus following transient global ischemia in rats. Experimental Neurology, 1999, pp. 444-450, vol. 158.
Donnahoo et al., Early kidney TNF-alpha expression mediates neutrophil infiltration and injury after renal ischemia-reperfusion, American Journal of Physiology, Sep. 1999, pp. R922-R929. vol. 277, No. 3, Pt. 2.
Eckardt et al., Hypoxia-induced accumulation of erythropoietin mRNA in isolated hepatocytes is inhibited by protein kinase C, Pflugers Archiv., 1994, pp. 21-30, vol. 426.
Engles et al., Exogenous human recombinant interleukin-10 attenuates hindlimb ischemia-reperfusion injury. Journal of Surgical Research, 1997, pp. 425-428, vol. 69.
Garkavtsev et al., Suppression of the novel growth inhibitor p33ING1 promotes neoplastic transformation, Nature Publishing Group, Dec. 14, 1996, pp. 415-420.
Garkavtsev et al., The candidate tumour suppressor p33ING1 cooperates with p53 in cell growth control, Nature, Jan. 15, 1998, pp. 295-298, vol. 391.
Gudkov et al., The role of p53 in determining sensitivity to radiotherapy. Nature Reviews. Feb. 2003. pp. 117-129, vol. 3.
Gudkov, Andrei V., Cancer drug discovery: the wisdom of imprecision, Nature Medicine, Dec. 2004, 1298-00, vol. 10, No. 12.
Gudkov, Andrei V., Converting p53 from a killer into a healer, Nature Medicine. Nov. 2002, pp. 1196-1198, vol. 8, No. 11.
http://www.rxlist.com/cgi/generic/chorionic.htm—RX List.com entry for hCG/Pregnyl, 2008.
Hierholzer et al., Essential role of induced nitric oxide in the initiation of the inflammatory response after hemorrhagic shock, J. Exp. Med., Mar. 1998, pp. 917-928, vol. 187, No. 6.
Huang et al., Ischemia-reperfusion and immediate T cell responses, Cellular Immunology, 2007, pp. 4-11. vol. 248.
Husek et al., Rapid screening of urinary proline-hydroxyproline dipeptide in bone turnover studies, Abstract, J. Chromatogr B Analyt Technol Biomed Life Sci., Feb. 5, 2002, pp. 169-174. vol. 767, No. 1.
Iyer et al., The transcriptional program in the response of human fibroblasts to serum, Science, Jan. 1999, pp. 83-87, vol. 283, No. 5398.
Kato et al., Reduced hepatic ischemia/reperfusion injury by IL-4: potential anti-inflammatory role of STAT6, Inflammation Research, Jun. 2000, pp. 275-279, vol. 49, No. 6.
Lane et al., Interleukin-10 reduces the systemic inflammatory response in a murine model of intestinal ischemia/reperfusion, Surgery, 1997, pp. 288-294, vol. 122, No. 2.
Le Moine et al., Cold liver ischemia-reperfusion injury critically depends on liver T cells and is improved by donor pretreatment with interleukin 10 in mice, Hepatology, 2000, pp. 1266-1274, vol. 31. No. 6.
Lutterova et al., Marked difference in tumor necrosis factor-alpha expression in warm ischemia- and cold ischemia-reperfusion of the rat liver. Cryobiology, 2000, pp. 301-314, vol. 41.
Manna et al., Human chorionic gonadotropin suppresses activation of nuclear transcription factor-kappa B and activator protein-1 induced by tumor necrosis factor, The Journal of Biological Chemistry, May 2000, pp. 13307-13314, vol. 275, No. 18.

NCBI Accession No. AAI06724. version Oct. 6, 2006.
Padmos et al., A discriminating messenger RNA signature for bipolar disorder formed by an aberrant expression of inflammatory genes in monocytes. Arch Gen Psychiatry, Apr. 2008, pp. 395-407. vol. 65. No. 4.
Pan et al., Bradykinin Stimulates NF-κB Activation and Interleukin 1β Gene Expression in Cultured Human Fibroblasts, J. Clin. Invest., Nov. 1996. pp. 2042-2049, vol. 98, No. 9. The American Society for Clinical Investigation, Inc.
Partial European Search Report for 02 763 111.8 dated Nov. 23, 2007.
PCT International Search Report and Written Opinion. PCT/NL2007/050092, dated Jul. 6, 2007.
PCT International Search Report, PCT/CA97/00568, dated Apr. 30, 1998.
Qin et al., Nuclear Factor kB Nuclear Translocation Upregulates c-Myc and p53 Expression during NMDA Receptor-Mediated Apoptosis in Rat Striatum, The Journal of Neuroscience, May 15, 1999, pp. 4023-4033. vol. 19, No. 10.
Quillan et al., Combinatorial diffusion assay used to identify topically active melanocyte-stimulating hormone receptor antagonists, PNAS, Mar. 1995, pp. 2894-2898, vol. 92. USA.
"RDT&E Budget item justification sheet" StartDateMarker 1999, EndDateMarker Retrieved from the Internet: URL:http://www.dtic.mil/descriptivesum/Y2000/OSD/PE0602787D.pdf>.
Redon et al., Global variation in number in the human genome. Nature, Nov. 23, 2006, pp. 444-454, vol. 444.
Riera et al., Neutrophils accentuate renal cold ischemia-reperfusion injury. Dose-dependent protective effect of platelet-activating factor receptor antagonist. The Journal of Pharmacology and Experimental Therapeutics, 1997, pp. 786-794, vol. 280, No. 2.
Rodriguez et al., Expression of human HLA-B27 transgene alters susceptibility to murine theiler's virus-induced demylenination, 1991. vol. 146. pp. 2596-2602.
Selzman et al., Interleukin-10 inhibits postinjury tumor necrosis factor-mediated human vascular smooth muscle proliferation, Journal of Surgical Research, 1998, pp. 352-356, vol. 80.
Sovak et al., Aberrant nuclear factor-kappa B/Rel expression and the pathogenesis of breast cancer, The Journal of Clinical Investigation, Dec. 1997, pp. 2952-2960, vol. 100, No. 12.
Strom et al., Small-molecule inhibitor of p53 binding to mitochondria protects mice from gamma radiation, Nature Chemical Biology, Sep. 2006. pp. 474-479. vol. 2, No. 9.
Szinicz. L., History of chemical and biological warfare agents, Abstract, Toxicology, Oct. 30, 2005, pp. 167-181, vol. 214, No. 3.
Thibonnier et al., Cytoplasmic and nuclear signaling pathways of VI-vascular vasopressin receptors, Regulatory Peptides. 1993, pp. 79-84, vol. 45.
Valore et al., Human b-Defensin-1: An antimicrobial Peptide of Urogenital Tissues, J. Clin. Invest., Apr. 1998. pp. 1633-1642, vol. 101, No. 8.
Wallraff et al.. Urinary Excretion of Amino Acids in Pregnancy, J. Clinc. Invest., 1950, pp. 1542-1544, vol. 29.
Wu et al., Gonadotropin-Releasing Hormone (GNRH) Cleavage Products are Involved in the Regulation of GNRH Gene Expression in the GTI-7 Neuronal Cell Line, Society for Neuroscience Abstracts, Nov. 4, 2000, pp. 7.8, XP009091566, vol. 26. No. 1-2.
U.S. Appl. No. 12/069,401, filed Feb. 8. 2008, Khan et al., Immunoregulatory Compositions.
U.S. Appl. No. 12/069,741, filed Feb. 12, 2008, Khan et al., Treatment of Trauma-Hemorrhage With Short Oligopeptides.
U.S. Appl. No. 12/074,020, filed Feb. 29, 2008, Khan et al., Oligopeptide Treatment of Ischemia-Reperfusion Injury.
U.S. Appl. No. 12/083,472, filed Jun. 27, 2008, Drexhage et al., Method to Diagnose or Screen for Inflammatory Diseases.
U.S. Appl. No. 12/288,935, filed Oct. 24, 2008, Benner et al., Control of Radiation Injury.
U.S. Appl. No. 12/383,849, filed Mar. 27, 2009, Khan et al., Compositions for Mucosal and Oral Administration Comprising HCG Fragments.
U.S. Appl. No. 12/386,061, filed Apr. 9, 2009, Khan et al., Methods and Uses for Protein Breakdown Products.
U.S. Appl. No. 12/386,135, filed Apr. 14, 2009, Khan et al., Gene Regulator.

(56) References Cited

OTHER PUBLICATIONS

Abeyama et al., A role of NF-κB-dependent gene transactivation in sunburn. The Journal of Clinical Investigation, vol. 105, No. 12, pp. 1751-1759, Jun. 2000.
Abraham, E., "Coagulation Abnormalities in Acute Lung Injury and Sepsis," Am. J. Respir. Cell Mol. Biol., 2000, pp. 401-404, vol. 22.
Adib-Conquy et al., "NF-κB Expression in Mononuclear Cells in Patients with Sepsis Resembles That Observed in Lipopolysaccharide Tolerance," Am. J. Respir. Crit. Care Med., 2000, pp. 1877-1883, vol. 162.
Agawal et al., Acute Renal Failure, American Family Physician, 2000, pp. 2077-88, vol. 61, corresponding to web version of p. 1-12.
Albini et al., "Old drugs as novel angiogenesis inhibitors: Preclinical studies with NAC, hCG, EGCG and somatostatin," Clinical & Experimental Metastasis, 1999, pp. 739, vol. 17.
Arima et al., "IL-2-Induced Growth of CD8+ T Cell Prolymphocytic Leukemia Cells Mediated by NF-kappaB Induction and IL-2 Receptor alpha Expression," Leukemia Research, 1998, pp. 265-273, vol. 22, No. 3.
Baeuerle et al., "Function and Activation of NF-κB in the Immune System," Annu. Rev. Immunol., 1994, pp. 141-179, vol. 12.
Bethea et al., "Traumatic Spinal Cord Injury Induces Nuclear Factor-κB Activation," The Journal of Neuroscience, May 1, 1998, pp. 3251-3260, vol. 18, No. 9.
Blackwell et al., "The Role of Nuclear Factor-κB in Cytokine Gene Regulation," Am. J. Respir. Cell Mol. Biol., 1997, pp. 3-9, vol. 17.
Bodfish et al., "Treating the Core Features of Autism: Are We There Yet?" Mental Retardation and Developmental Disabilities Research Reviews, 2004, pp. 318-326, vol. 10.
Bradham et al., Activation of nuclear factor- κB during orthotopic liver transplantation in rats is protective and does not require Kuppfer cells, Liver Transplantation and Surgery, Jul. 1999, pp. 282-293, vol. 5, No. 4.
Brown et al., "Two Forms of NF-kappaB1 (p105/p50) in Murine Macrophages: Differential Regulation by Lipopolysaccharide, Interleukin-2, and Interferon-gamma," Journal of Interferon and Cytokine Research, 1997, pp. 295-306, vol. 17.
Christman et al., "Nuclear factor kappaB: a pivotal role in the systemic inflammatory response syndrome and new target for therapy," Intens Care Med, 1998, pp. 1131-1138, vol. 24.
Connelly et al., "Biphasic Regulation of NF-κB Activity Underlies the Pro- and Anti-inflammatory Actions of Nitric Oxide," The Journal of Immunology, 2001, pp. 3873-3881, 166, The American Association of Immunologists, USA.
Cook et al., Modified total lymphoid irradiation and low dose coricosteroids in progressive multiple sclerosis, Journal of Neurological Sciences, vol. 152, pp. 172-181, 1997.
Cui et al., Am. J. Physiol. Integr. Comp. Physiol., 2004, pp. R699-R709, vol. 286.
De Saizieu et al.. Journal of Bacteriology, vol. 182, No. 17, pp. 4696-4703, Sep. 2000.
Dechend et al., Oncogene, vol. 18, pp. 3316-3323, 1999.
Dwinnell et al., Atlas of Diseases of the Kidney, Blackwell Sciences, 1999, pp. 12.1-12.12, Ch. 12.
Emmel et al., "Cyclosporin a Specifically Inhibits Function of Nuclear Proteins Involved in T Cell Activation," Science, Dec. 22, 1989, pp. 1617-1620, vol. 246.
Epinat et al., "Diverse agents act at multiple levels to inhibit the Rel/NF-kappaB signal transduction pathway," Oncogene, 1999, pp. 6896-6909, vol. 18.
Fassio et al., Transforming Growth Factor Alpha and Its Receptor in Neural Retina, Investigative Ophthalmology & Visual Science, Sep. 1989, pp. 1916-1922, vol. 30, No. 9.
Faust et al., "Disseminated intravascular coagulation and purpura fulminans secondary to infection," Bailliere's Clinical Haematology, 2000, 179-197, vol. 13. No. 2.
Flores et al., NFkappaB and AP-1 DNA binding activity in patients with multiple sclerosis. J. Neuroimmunol. vol. 135, No. 1-2, pp. 141-147, Feb. 2003.

Friedlander, "Tackling anthrax," Nature, Nov. 8, 2001, pp. 160-61, vol. 414.
GenBank Accession No. NP_000728, GI: 4502789, publicly available Apr. 2007.
Han et al., Cholecystokinin induction of mob-1 chemokine expression in pancreatic acinar cells requires NF-kappaB activation, American Journal of Physiology, Jul. 1999, vol. 277, pp. C74-C82.
Ichiyama et al., Systemically administered alpha-melanocyte-stimulating peptides inhibit NF-kappaB activation in experimental brain inflammation, Brain Research, Jul. 1999, pp. 31-37, vol. 836.
Ivanov et al., "Hemoglobin as a Source of Endogenous Bioactive Peptides: The Concept of Tissue-Specific Peptide Pool," Biopolymers, 1997, pp. 171-188, vol. 39.
Jimenez-Garza et al., "Early Effects of Modulating Nuclear factor-kappaB Activation on Traumatic Spinal Cord Injury in Rats," Ann. N. Y Acad. Sci., 2005, pp. 148-150, vol. 1053.
Jyonouchi et al., "Proinflammatory and regulatory cytokine production associated with innate and adaptive immune responses in children with autism spectrum disorders and developmental regression," J Neuroim., 2001, pp. 170-179, vol. 120.
Kachra et al., "Low Molecular Weight Components but Not Dimeric HCG Inhibit Growth and Down-Regulate AP-1 Transcription Factor in Kaposi's Sarcoma Cells," Endocrinology, 1997, pp. 4038-4041, vol. 138, No. 9.
Kalns et al., Biochem. Biophys. Res. Comm., 2002, pp. 41-44, vol. 292.
Kalns et al., Biochem. Biophys. Res. Comm., 2002, pp. 506-09, vol. 297.
Kanungo et al., "Advanced Maturation of Heteropneustes Fossilis (Bloch) by Oral Administration of Human Chorionic Gonadotropin," J. Adv. Zool., 1999, pp. 1-5, vol. 20.
Keeton and Gould, Biological Science, 5th Ed., New York, W.W. Norton & Company, Inc. 1993, p. 4.
Keller et al., "Human Chorionic Gonadotropin (hCG) Is a Potent Angiogenic Factor for Uterine Endothelial Cells in Vitro," Placenta, Jul. 1999, pp. A37, vol. 20, No. 5-6.
Khan et al., "Inhibition of Diabetes in NOD Mice by Human Pregnancy Factor," Human Immunology, Dec. 2001, pp. 1315-1323, vol. 62, No. 12.
Khan et al., "Inhibition of Septic Shock in Mice by an Oligopeptide From the β-Chain of Human Chorionic Gonadtrophin Hormone," Human Immunology, Jan. 2002, pp. 1-7, vol. 63, No. 1.
Khavinson et al., Gerontological Aspects of Genome Peptide Regulation, 2005, S. Karger AG, Basel, Switzerland.
Khavinson et al., "Effects of Livagen Peptide on Chromatin Activation in Lymphocytes from Old People," Bulletin of Experimental Biology and Medicine, Oct. 2002, pp. 389-392, vol. 134, No. 4.
Khavinson et al., "Effects of Short Peptides on Lymphocyte Chromatin in Senile Subjects," Bulletin of Experimental Biology and Medicine, Jan. 2004, pp. 78-81, vol. 137, No. 1.
Khavinson et al., "Epithalon Peptide Induces Telomerase Activity and Telomere Elongation in Human Somatic Cells," Bulletin of Experimental Biology and Medicine, Jun. 2003, pp. 590-592, vol. 135, No. 6.
Khavinson et al., "Inductive Activity of Retinal Peptides," Bulletin of Experimental Biology and Medicine, Nov. 2002, pp. 482-484, vol. 134, No. 5.
Khavinson et al., "Mechanisms Underlying Geroprotective Effects of Peptides," Bulletin of Experimental Biology and Medicine, Jan. 2002, pp. 1-5, vol. 133, No. 1.
Khavinson et al., "Peptide Promotes Overcoming of the Division Limit in Human Somatic Cell," Bulletin of Experimental Biology and Medicine, May 2004, pp. 503-506, vol. 137, No. 5.
Kidd et al., "Autism, An Extreme Challenge to Integrative Medicine. Part II: Medical Management," Alternative Medicine Review, 2002, pp. 472-499, vol. 7, No. 6.
Kronfol et al., "Cytokines and the Brain: Implications for Clinical Psychiatry," Am. J. Psychiatry, May 2000, pp. 683-694, vol. 157, No. 5.
Lang et al., "Induction of apoptosis in Kaposi's sarcoma spindle cell cultures by the subunits of human chorionic gonadtropin," AIDS, 1997, pp. 1333-40, vol. 11, No. 11.

(56) References Cited

OTHER PUBLICATIONS

Li et al., "NF-kappaB Regulation in the Immune System," Nature Reviews/Immunology, Oct. 2002, pp. 725-734, vol. 2.
Lin et al., The Journal of Biological Chemistry, vol. 270, No. 24, pp. 14255-14258, Jun. 1995.
Lunardi-Iskandar et al., "Effects of a urinary factor from women in early pregnancy on HIV-a, SIV and associated disease," Nature Medicine, pril 1998, pp. 428-434, vol. 4, No. 4.
Malek-Ahmadi, P., "Role of Cytokines in Psychopathology: Therapeutic Implications," Drug News Prospects, Jun. 1998, pp. 271-276, vol. 11, No. 5.
Malyak et al., Characterization of a Low Molecular Weight Isoform of IL-1 Receptor Antagonist, The Journal of Immunology, 1998, pp. 1997-2003, vol. 161.
McBean et al., "Rodent Models of Global Cerebral Ischemia: A Comparison of Two-Vessel Occlusion and Four-Vessel Occlusion," Gen. Pharmac., 1998, pp. 431-434, vol. 30, No. 4.
McDonald et al., "Interleukin-15 (IL-15) Induces NF-kappaB Activation and IL-8 Production in Human Neutrophils," Blood, Dec. 15, 1998, pp. 4828-4835, vol. 92, No. 12.
MedlinePlus, Medical Encyclopedia: autoimmune disorders (www.nlm.gov/medlineplus/ency/article/000816.htm), 2007.
Medzhitov, "Toll-like Receptors and Innate Immunity," Nature Reviews/Immunology, Nov. 2001, pp. 135-45, vol. 1.
Merck Index, 17th ed. 1999, pp. 1145-1146, 1841-1848, 2539, 2551.
Merriam-Webster Medical Dictionary, 1994, p. 82.
Moayeri et al., Journal of Clinical Investigation, Sep. 2003, pp. 670-82, vol. 112, No. 5.
Morozov et al., "Natural and Synthetic Thymic Peptides as Therapeutics for Immune Dysfunction," Int. J. Immunopharmac., 1997, pp. 501-505, vol. 19, No. 9/10.
Muchmore et al., "Immunoregulatory Properties of Fractions from Human Pregnancy Urine: Evidence that Human Chorionic Gonadotropin is not Responsible," The Journal of Immunology, Mar. 1997, pp. 881-886, vol. 118, No. 3.
Muchmore et al., "Purification and Characterization of a Mannose-Containing Disaccharide Obtained from Human Pregnancy Urine," Journal of Experimental Medicine, Dec. 1984, pp. 1672-1685, vol. 160.
Neely et al., "Then and now: Studies using a burned mouse model reflect trends in burn research over the past 25 years," Burns, 1999, pp. 603-609, vol. 25.
Ngo et al., The protein folding problem and tertiary structure prediction, 1994, pp. 492-494.
Ohlsson et al., Interleukin-1 Receptor Antagonist Reduces Mortality from Endotoxin Shock, Nature, Dec. 6, 1990, pp. 550-552, vol. 348.
Oka et al., Immunosuppression in organ transplantation, Japanese Journal of Pharmacology, vol. 71, No. 2, pp. 89-100, Jun. 1996.
Olszyna et al., Levels of Inhibitors of Tumor Necrosis Factor Alpha and Interleukin 1b in Urine and Sera of Patients with Urosepsis, Infection and Immunity, Aug. 1998, pp. 3527-3534.
Patil et al., "The Study of the Effect of Human Chorionic Gonadotrophic (HCG) Hormone on the Survival of Adrenal Medulla Transplant in Brain. Preliminary Study," ACTA Neurochir (WIEN), 1987, pp. 76-78, vol. 87.
PCT International Search Report, International Application No. PCT/NL02/00639, mailed Aug. 4, 2003.
PCT International Search Report, PCT/EP2005/003707, dated Jul. 5, 2005.
PCT International Search Report, PCT/NL01/00259, dated Dec. 18, 2001.
Pellizzari et al., FEBS Letters, 1999, pp. 199-204, vol. 462.
Rohrig et al., "Growth-stimulating Influence of Human Chorionic Gonadotropin (hCG) on Plasmodium falciparum in vitro," Zentralblatt Bakt, 1999, pp. 89-99, vol. 289.
Samaniego et al., "Induction of Programmed Cell Death in Kaposi's Sarcoma Cells by Preparations of Human Chorionic Gonadotropin," Journal of the National Cancer Institute, Jan. 20, 1999, pp. 135-143, vol. 91, No. 2.
Sharma, Septic Shock, (visited Sep. 27, 2007 <http://www.emedicine.corn/MED/topic2101.htm>.
Slater et al., "Decreased Mortality of Murine Graft-Versus-Host Disease by Human Chorionic gonadotropin," Transplantation, Jan. 1977, pp. 103-104, vol. 23, No. 1.
Smith et al., "Recent developments in drug therapy for multiple sclerosis," Multiple Sclerosis, 1999, pp. 110-120, vol. 5.
Tak et al., "NF-kappaB: a key role in inflammatory diseases," J Clin Invest., 2001, pp. 7-11, vol. 107.
Tan et al., "The role of activation of nuclear factor-kappa B of rat brain in the pathogenesis of experimental allergic encephalomyelitis," Acta Physiol Sinica, 2003, pp. 58-64, vol. 55.
Tovey et al., "Mucosal Cytokine Therapy: Marked Antiviral and Antitumor Activity," J. Interferon Cytokine Res., 1999, pp. 911-921, vol. 19.
Traystman, R., "Animal Models of Focal and Global Cerebral Ischemia," ILAR Journal, 2003, pp. 85-95, vol. 44, No. 2.
Weinberger et al., "Mechanisms Mediating the Biologic Activity of Synthetic Proline, Glycine, and Hydroxyproline Polypeptides in Human Neurophils," Mediators of Inflammation, 2005, pp. 31-38, vol. 1.
Wulczyn et al., "The NF-κB/Rel and IkB gene families: mediators of immune response and inflammation," J. Mol. Med., 1996, pp. 749-769, vol. 74, No. 12.
Yamamoto et al., "Role of the NF-κB Pathway in the Pathogenesis of Human Disease States," Current Molecular Medicine, Jul. 2001, pp. 287-296, vol. 1, No. 3.
Yang et al., "Increased cortical nuclear factor κB (NF-κB) DNA binding activity after traumatic brain injury in rats," Neuroscience Letters, 1995, pp. 101-104, vol. 197.
Zhou et al., Transplantation tolerance in NF-κB-impaired mice is not due to regulation but is prevented by transgenic expression of Bcl-xL. The Journal of Immunology, vol. 174, No. 6, pp. 3447-3453, Mar. 2005.

* cited by examiner

```
SEQUENCE LISTING

<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 1

Met Thr Arg Val
1

<210> SEQ ID NO 2
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 2

Ala Gln Gly Val
1

<210> SEQ ID NO 3
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 3

Leu Gln Gly Val
1

<210> SEQ ID NO 4
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 4

Leu Ala Gly Val
1
```

```
<210> SEQ ID NO 5
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 5

Val Leu Pro Ala Leu Pro Gln
1               5

<210> SEQ ID NO 6
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 6

Val Leu Pro Ala Leu Pro
1               5

<210> SEQ ID NO 7
<211> LENGTH: 17
<212> TYPE: PRT
<213> ORGANISM: Artificial Sequence
<220> FEATURE:
<223> OTHER INFORMATION: Synthesized Peptide

<400> SEQUENCE: 7

Met Thr Arg Val Leu Gln Gly Val Leu Pro Ala Leu Pro Gln Val Val
1               5                   10                  15

Cys

<210> SEQ ID NO 8
<211> LENGTH: 4
<212> TYPE: PRT
<213> ORGANISM: Homo sapiens

<400> SEQUENCE: 8

Gln Val Val Cys
1
```

OLIGOPEPTIDE ACETATE AND FORMULATIONS THEREOF

CROSS-REFERENCE TO RELATED APPLICATIONS

This application is a continuation-in-part of U.S. patent application Ser. No. 10/409,668, filed Apr. 8, 2003 now abandoned, and a continuation-in-part of U.S. patent application Ser. No. 11/037,972, filed Jan. 18, 2005 now U.S. Pat. No. 7,820,617, which is a continuation of U.S. patent application Ser. No. 09/821,380, filed Mar. 29, 2001, now U.S. Pat. No. 6,844,315 B2, which is a continuation-in-part of earlier U.S. patent application Ser. No. 09/716,777, filed Nov. 20, 2000, now U.S. Pat. No. 6,921,751 B1, which is a continuation of co-pending International Application No. PCT/NL99/00313, filed May 20, 1999, designating the United States of America, which itself claims priority from EP 98201695.8, filed on May 20, 1998, and EP 98202706.2, filed on Aug. 12, 1998, the contents of the entirety of all of which are incorporated herein by this reference. This application is also a continuation-in-part of U.S. patent application Ser. No. 10/262,522, filed Sep. 30, 2002, now U.S. Reissue Pat. No. RE43140, issued Jan. 24, 2012, which is a reissue of U.S. Pat. No. 7,365,155, issued Apr. 29, 2008, which is a continuation of International Application No. PCT/NL01/00259, filed Mar. 29, 2001, designating the United States of America, and published as International PCT Publication No. WO 01/72831 A1, which International Publication itself claims priority from EP 00201139, filed on Mar. 29, 2000.

TECHNICAL FIELD

The invention relates generally to biotechnology and medicine, and, more particularly, to anti-inflammatory activity found in short (tri- to hepta-meric) peptides derived from human chorionic gonadotropin particularly AQGV (SEQ ID NO:2 of the incorporated herein SEQUENCE LISTING) and LQGV (SEQ ID NO:3), as pharmaceutical compounds.

BACKGROUND

Human chorionic gonadotropin ("hCG") is a heterodimeric placental glycoprotein hormone required in pregnancy. In the urine of human pregnancy and in commercial hCG preparations, it occurs in a variety of forms, including breakdown products. Several investigators have studied the effects of heterodimeric hCG and its variants on the immune system because of their putative role in preventing the rejection of the fetal allograft during pregnancy. Several reports have suggested modulation of the immune system by intact hormone, but such effects of breakdown products have not been reported.

Khan et al., *Hum Immunol.* 2002 January; 63(1):1-7, reported inhibition of septic shock in mice by a 6-mer oligopeptide (VLPALP (SEQ ID NO:6)) derived from the beta-chain of human chorionic gonadotropin hormone. A single treatment with this hexapeptide after high dose lipopolysaccharide ("LPS") injection inhibited septic shock in mice. Benner and Khan (*Scand J Immunol.* 2005 July; 62 Suppl 1:62-6) studied the possible immunological activity of the in vivo liberated peptide fragments originating from nicking of the sequence MTRVLQGVLPALPQVVC (residues 41-57) of loop 2 of the beta-subunit of hCG (SEQ ID NO:7). It is there reported that several of 3-7 amino acid-long peptides taken from loop 2 of the beta-subunit—and alanine-replacement peptides derived of some—displayed significant anti-inflammatory activity as measured by the inhibition of septic shock syndrome in mice. Selection was based on the known preferential cleavage sites of the sequence MTRVLQGVLPALPQVVC (residues 41-57) of loop 2 of the beta-subunit of hCG (SEQ ID NO:7).

(Cole et al., *J Clin Endocr Metab* 1993; 76:704-710; Alfthan H, Stenman U H. *Mol Cell Endocrinol* 1996; 125:107-120; Kardana A, et al., *Endocrinology* 1991; 129:1541-1550; Cole et al., *Endocrinology* 1991; 129:1559-1567; Birken S, Maydelman Y, Gawinowicz M A. *Methods* 2000; 21:3-14) The peptides LQGV (SEQ ID NO:3) and AQGV (SEQ ID NO:2) were selected for synthesis, of which the results are presented here.

BRIEF SUMMARY OF THE INVENTION

Khan et al., *Hum Immunol.* 2002 January; 63(1):1-7, reported inhibition of septic shock in mice by a 6-mer oligopeptide (VLPALP (SEQ ID NO:6)) derived from the beta-chain of human chorionic gonadotropin hormone. A single treatment with this hexapeptide after high dose LPS injection inhibited septic shock in mice. Here, we show that several other short (from trimeric peptides up) peptides derived from the beta chain of hCG, and modifications of some of said peptides obtained by alanine substitution of single amino acids, have similar anti-inflammatory activity. Furthermore, we provide our rational for selecting two of these (AQGV (SEQ ID NO:2) and LQGV (SEQ ID NO:3)) as therapeutic compounds for treatment of conditions such as human acute inflammatory conditions (e.g., sepsis).

In certain embodiments, the invention provides an acetate of tetrapeptide, wherein the tetrapeptide is AQGV (SEQ ID NO:2) and/or LQGV (SEQ ID NO:3). In certain embodiments, the acetate of a tetrapeptide is an acetate salt of the tetrapeptide. In a further embodiment the acetate of a tetrapeptide is an acetate ester of the tetrapeptide.

An additional aspect of the invention provides a pharmaceutical composition comprising acetate of a tetrapeptide, wherein the tetrapeptide is SEQ ID NO:2 and/or SEQ ID NO:3 and a pharmaceutically acceptable carrier, adjuvant, or excipient.

A further aspect of the invention provides a method of treating an acute inflammatory condition in a subject comprising administering the acetate of a tetrapeptide SEQ ID NO:3 and/or SEQ ID NO:2 to a subject having an acute inflammatory condition in an amount efficacious to reduce the inflammation in the subject as may be determined by a decrease in serum IL-6 levels in the subject. An additional aspect of the invention provides a method of treating an acute inflammatory condition in a subject comprising administering to the subject a pharmaceutical composition of the invention in an amount efficacious to reduce the inflammation in the subject as may be determined by a decrease in serum IL-6 levels in the subject. In certain embodiments, the acute inflammatory condition is sepsis.

DETAILED DESCRIPTION OF EXAMPLE EMBODIMENTS THE INVENTION

Figure 1:
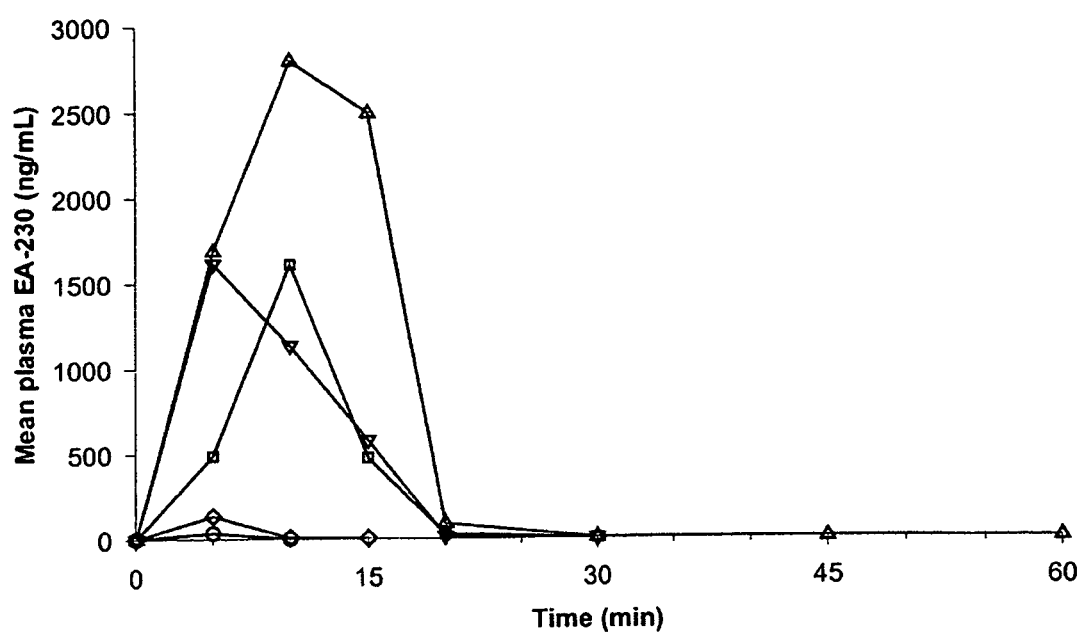
FIG. 1. is a graph depicting mean EA-230 concentrations in the plasma of subjects who received various dosages of EA-230 at various times after administration. Circles indicate an initial dose of 1 mg/kg; diamonds indicate an initial dose of 3 mg/kg; squares indicate an initial dose of 10 mg/kg; upright triangles indicate an initial dose of 30 mg/kg; and inverted triangles indicate a dosage of LPS followed by initial dose of 10 mg/kg EA-230.
Figure 2A:
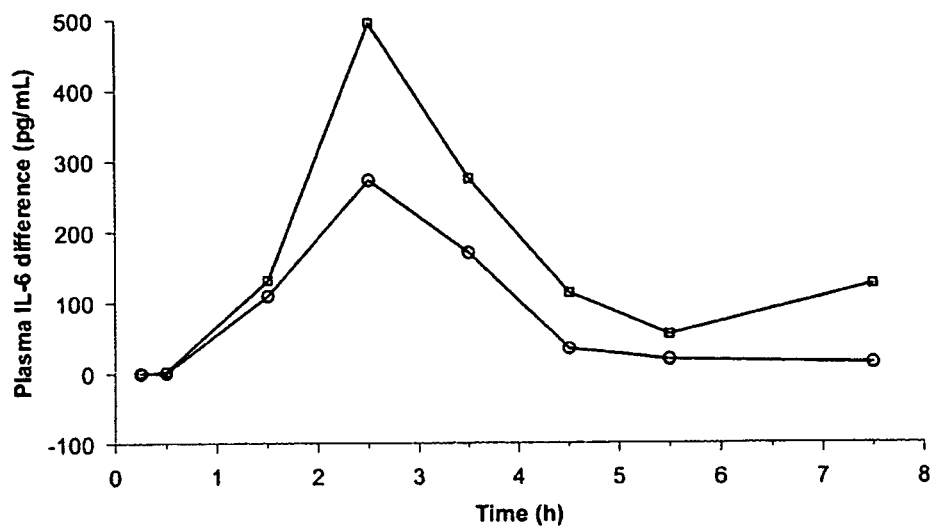
FIGS. 2A and 2B. are graphs depicting average changes in the concentration of IL-6 and IL-8 in the plasma of subjects respectively. All subjects were treated with 4 ng/kg LPS 30 minutes prior to administration of a placebo (squares) or 10 mg/kg EA-230 (circles).
Figure 2B:
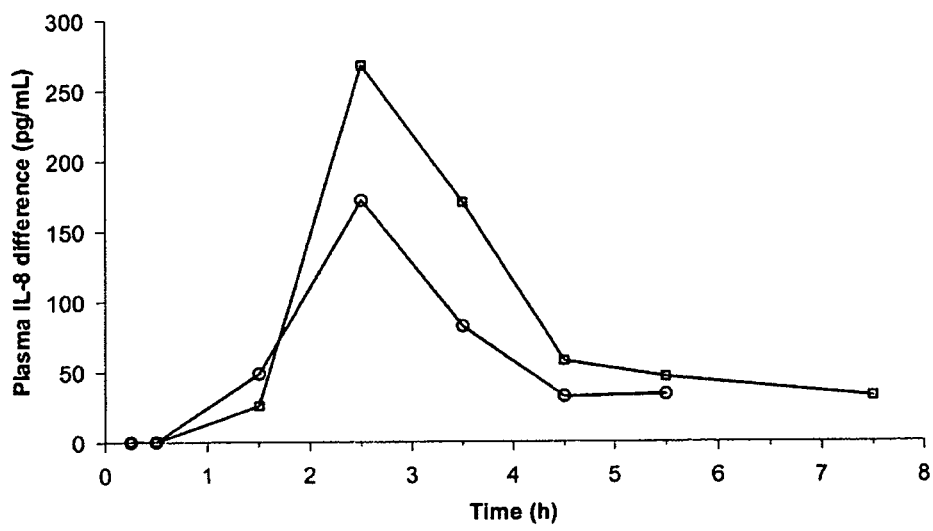

As used herein, a "purified, synthetic or isolated" peptide is one that has been purified from a natural or biotechnological source, or, more preferably, is synthesized as described herein.

As used herein, the phrases "treatment of an acute inflammatory condition," and "management of an acute inflammatory condition" are used interchangeably and do not necessarily imply the realization of a complete cure of the condition. These phrases include reduction of the symptoms of the underlying disease and/or reduction of one or more of the underlying cellular, physiological, or biochemical indicators, causes, risks or mechanisms associated with an acute inflammatory condition, including reduction of such symptoms or underlying indicators, causes, risks or mechanisms to below detectable levels. "Reduced," as used in this context, means a reduction in characteristic indicators, causes or mechanisms of the disease state or reduction in a risk of an associated disease state relative to the untreated state of the disease, including, but not limited to cellular, physiological, or biochemical indicators or risks of the diseased state or associated with the disease state.

As used herein, an "effective amount" means an amount of a composition administered to a subject that is effective to improve, prevent, reduce the symptoms of, or treat the disease condition in the subject.

As used herein, an "acute inflammatory condition" refers to a disease (or diseases) commonly associated with a one time inflammatory event. Examples of acute inflammatory conditions include, but are not limited to, sepsis, septic shock, anaphylactic shock, and hyper-acute transplant rejection.

"Composition," as used herein, refers to chemical compounds that contain or consist of the oligopeptide. The oligopeptide may be isolated before inclusion within the composition. The oligopeptide most preferably consists of three (3) to six (6) amino acids. Examples of an oligopeptide include, but are not limited to, SEQ ID NO:2 and SEQ ID NO:3.

For instance, a preferred compound could, in certain embodiments be: NT A Q G V CT wherein NT at the N-terminus is selected from the group of H—, CH3-, an acyl group, or a general protective group; and CT at the C-terminus is selected from the group of small (e.g., 1 to 5 amino acids) peptides, —OH, —OR$^1$, —NH$_2$, —NHR$^1$, —NR$^1$R$^2$, or —N(CH$_2$)$_{1-6}$NR$^1$R$^2$, wherein R$^1$ and R$^2$, when present, are independently selected from H, alkyl, aryl, (ar)alkyl, and wherein R$^1$ and R$^2$ can be cyclically bonded to one another.

"Alkyl" as used herein, is preferably a saturated branched or unbranched hydrocarbon having one to six carbon atoms, for example, methyl, ethyl, and isopentyl.

"Aryl" as used herein, is an aromatic hydrocarbon group, preferably having 6 to 10 carbon atoms, such as phenyl or naphthyl.

"(Ar)alkyl" as used herein, is an arene group (having both aliphatic and aromatic portions), preferably having 7 to 13 carbon atoms such as benzyl, ethylbenzyl, n-propylbenzyl, and isobutylbenzyl.

"Oligopeptide" as used herein, are peptides having from 3 to 12 amino acids joined together by peptide bonds. Equivalent to oligopeptides are compounds having the same or equivalent side chains as the particular amino acids used in an oligopeptide, and arranged sequentially in the same order as the peptides, but joined together by non-peptide bonds, e.g., by isosteric linkages such as the keto isostere, hydroxy isostere, diketo isostere, or the keto-difluoromethylene isostere.

"Composition" also includes, for example, an acceptable salt, counter ion, or ester of the oligopeptide or a labeled oligopeptide. As used herein, "acceptable salt" refers to salts that retain the desired activity of the oligopeptide or equivalent compound, but preferably do not detrimentally affect the activity of the oligopeptide or other component of a system in which uses the oligopeptide. Examples of such salts (or counter ions) are acid addition salts formed with inorganic acids, for example, hydrochloric acid, hydrobromic acid, sulfuric acid, phosphoric acid, nitric acid, and the like. Salts may also be formed with organic acids such as, for example, acetic acid, trifluoroacetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts may be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (e.g., a zinc tannate salt). Non-limiting examples of compositions according the invention include acetate salts or esters of AQGV (SEQ ID NO:2) and/or LQGV (SEQ ID NO:3).

Such a composition may be administered to the subject parenterally or orally. Such a composition may consist essentially of oligopeptide and PBS. It is preferred that the oligopeptide is of synthetic origin. Suitable treatment for example entails administering the oligopeptide in the composition to the patient intravenously in an amount of from about 0.1 to about 35 mg/kg body mass of the subject. It may be useful that the pharmaceutical composition consists essentially of from one to three different oligopeptides.

The thus developed chemical entity can be administered and introduced in-vivo systemically, topically, or locally. The peptide, or its modification or derivative, can be administered as the entity as such or as a pharmaceutically acceptable acid- or base addition salt, formed by reaction with an inorganic acid (such as hydrochloric acid, hydrobromic acid, perchloric acid, nitric acid, thiocyanic acid, sulfuric acid, and phosphoric acid); or with an organic acid (such as formic acid, acetic acid, propionic acid, glycolic acid, lactic acid, pyruvic acid, oxalic acid, malonic acid, succinic acid, maleic acid, and fumaric acid); or by reaction with an inorganic base (such as sodium hydroxide, ammonium hydroxide, potassium hydroxide); or with an organic base (such as mono-, di-, trialkyl and aryl amines and substituted ethanolamines). A selected peptide and any of the derived entities may also be conjugated to sugars, lipids, other polypeptides, nucleic acids and PNA; and function in-situ as a conjugate or be released locally after reaching a targeted tissue or organ.

A "substitution" with regard to the various amino acids generally relate to substituting a group such as alkoxy, halogen, hydroxy, nitro, or lower alkyl onto an aromatic ring for hydrogen that would usually be present. Substitutions can also be made on the alkyl chain connecting the aromatic portion to the peptide backbone, with, for instance lower alkyl groups substituting for hydrogen. Still further substitutions can be made at the alpha position of an amino acid, also using an alkyl group.

Preferred substitutions involve the use of fluorine or chlorine as a halogen, and methoxy as an alkoxy group. With regard to alkyl and lower alkyl, generally alkyl groups having fewer (1 to 3) carbon atoms are preferred.

The compounds according to the general formula may be prepared in a manner conventional for such compounds. To that end, suitably N alpha protected (and side-chain protected if reactive side-chains are present) amino acid derivatives or peptides are activated and coupled to suitably carboxyl protected amino acid or peptide derivatives either in solution or on a solid support. Protection of the alpha-amino functions generally takes place by urethane functions such as the acid-labile tertiary-butyloxycarbonyl group ("Boc"), benzyloxycarbonyl ("Z") group and substituted analogs or the base-labile 9-fluoremyl-methyloxycarbonyl ("Fmoc") group. The Z group can also be removed by catalytic hydrogenation. Other suitable protecting groups include the Nps, Bmv, Bpoc, Aloc, MSC, etc. A good overview of amino protecting groups is given in *The peptides, Analysis, Synthesis, Biology*, Vol. 3 E. Gross and J. Meienhofer, eds. (Academic Press, New York, 1981). Protection of carboxyl groups can take place by ester formation, for example, base-labile esters like methyl or ethyl, acid labile esters like tert. butyl or, substituted, benzyl esters or hydrogenolytically. Protection of side-chain functions like those of lysine and glutamic or aspartic acid can take place using the aforementioned groups. Protection of thiol, and although not always required, of guanidino, alcohol and imidazole groups can take place using a variety of reagents such as those described in *The Peptides, Analysis, Synthesis, Biology, id.* or in *Pure and Applied Chemistry*, 59(3), 331-344 (1987). Activation of the carboxyl group of the suitably protected amino acids or peptides can take place by the azide, mixed anhydride, active ester, or carbodiimide method especially with the addition of catalytic and racemization-suppressing compounds like 1-N—N-hydroxybenzotriazole, N-hydroxysuccinimide, 3-hydroxy-4-oxo-3,4-dihydro-1,2,3,-benzotriazine, N-hydroxy-5norbornene-2,3-dicar-boxyimide. Also the anhydrides of phosphorus based acids can be used. See, e.g., *The Peptides, Analysis, Synthesis, Biology,* supra and *Pure and Applied Chemistry,* 59(3), 331-344 (1987).

It is also possible to prepare the compounds by the solid phase method of Merrifield. Different solid supports and different strategies are known see, e.g., Barany and Merrifield in *The Peptides, Analysis, Synthesis, Biology*, Vol. 2, E. Gross and J. Meienhofer, eds. (Acad. Press, New York, 1980), Kneib-Cordonier and Mullen *Int. J. Peptide Protein Res.*, 30, 705-739 (1987) and Fields and Noble *Int. J. Peptide Protein Res.*, 35, 161-214 (1990). The synthesis of compounds in which a peptide bond is replaced by an isostere, can, in general, be performed using the previously described protecting groups and activation procedures. Procedures to synthesize the modified isosteres are described in the literature e.g., for the —$CH_2$—NH— isostere and for the —CO—$CH_2$— isostere.

Removal of the protecting groups, and, in the case of solid phase peptide synthesis, the cleavage from the solid support, can take place in different ways, depending on the nature of those protecting groups and the type of linker to the solid support. Usually deprotection takes place under acidic conditions and in the presence of scavengers. See, e.g., volumes 3, 5 and 9 of the series on *The Peptides Analysis, Synthesis, Biology,* supra.

Another possibility is the application of enzymes in synthesis of such compounds; for reviews see, e.g., H. D. Jakubke in *The Peptides, Analysis, Synthesis, Biology*, Vol. 9, S. Udenfriend and J. Meienhofer, eds. (Acad. Press, New York, 1987).

Although possibly not desirable from an economic point of view, oligopeptides according to the invention could also be made according to recombinant DNA methods. Such methods involve the preparation of the desired oligopeptide thereof by means of expressing recombinant polynucleotide sequence that codes for one or more of the oligopeptides in question in a suitable microorganism as host. Generally the process involves introducing into a cloning vehicle (e.g., a plasmid, phage DNA, or other DNA sequence able to replicate in a host cell) a DNA sequence coding for the particular oligopeptide or oligopeptides, introducing the cloning vehicle into a suitable eucaryotic or prokaryotic host cell, and culturing the host cell thus transformed. When a eucaryotic host cell is used, the compound may include a glycoprotein portion.

As used herein, a "functional analogue" or "derivative" of a peptide includes an amino acid sequence, or other sequence monomers, which has been altered such that the functional properties of the sequence are essentially the same in kind, not necessarily in amount. An analogue or derivative can be provided in many ways, for instance, through "conservative amino acid substitution." Also peptidomimetic compounds can be designed that functionally or structurally resemble the original peptide taken as the starting point but that are for example composed of non-naturally occurring amino acids or polyamides. With a "conservative amino acid substitution," one amino acid residue is substituted with another residue with generally similar properties (size, hydrophobicity), such that the overall functioning is likely not to be seriously affected. However, it is often much more desirable to improve a specific function. A derivative can also be provided by systematically improving at least one desired property of an amino acid sequence. This can, for instance, be done by an Ala-scan and/or replacement net mapping method. With these methods, many different peptides are generated, based on an original amino acid sequence but each containing a substitution of at least one amino acid residue. The amino acid residue may either be replaced by alanine (Ala-scan) or by any other amino acid residue (replacement net mapping). This way, many positional variants of the original amino acid sequence are synthesized. Every positional variant is screened for a specific activity. The generated data are used to design improved peptide derivatives of a certain amino acid sequence.

A derivative or analogue can also be, for instance, generated by substitution of an L-amino acid residue with a D-amino acid residue. This substitution, leading to a peptide that does not naturally occur in nature, can improve a property of an amino acid sequence. It is, for example, useful to provide a peptide sequence of known activity of all D-amino acids in retro inversion format, thereby allowing for retained activity and increased half-life values. By generating many positional variants of an original amino acid sequence and screening for a specific activity, improved peptide derivatives comprising such D-amino acids can be designed with further improved characteristics.

A person skilled in the art is well able to generate analogous compounds of an amino acid sequence. This can, for instance, be done through screening of a peptide library. Such an analogue has essentially the same functional properties of the sequence in kind, not necessarily in amount. Also, peptides or analogues can be circularized, for example, by providing them with (terminal) cysteines, dimerized or multimerized, for example, by linkage to lysine or cysteine or other compounds with side-chains that allow linkage or multimerization, brought in tandem- or repeat-configuration, conjugated or otherwise linked to carriers known in the art, if only by a labile link that allows dissociation. Synthetic versions of these oligopeptides as described above, and functional analogues or derivatives or breakdown products, are herein provided to be used in methods to the treatment of radiation injury and subsequent disease.

The term "pharmaceutical composition", as used herein, includes both the active composition alone or a composition containing the composition of the invention together with a pharmaceutically acceptable carrier, diluent or excipient. Acceptable diluents of an oligopeptide as described herein in the detailed description are for example physiological salt solutions or phosphate buffered salt solutions. In certain embodiments, an oligopeptide or composition is administered in an effective concentration to an animal or human systemically, for example, by intravenous, intramuscular or intraperitoneal administration. Another way of administration comprises perfusion of organs or tissue, be it in vivo or ex vivo, with a perfusion fluid comprising an oligopeptide or composition according to the invention. The administration may be done as a single dose, as a discontinuous sequence of various doses, or continuously for a period of time sufficient to permit substantial modulation of gene expression. In the case of a continuous administration, the duration of the administration may vary depending upon a number of factors that would readily be appreciated by those skilled in the art.

The administration dose of the active molecule may be varied over a fairly broad range. The concentrations of an active molecule that can be administered would be limited by efficacy at the lower end and the solubility of the compound at the upper end. The optimal dose or doses for a particular patient should and can be determined by the physician or medical specialist involved, taking into consideration well-known relevant factors such as the condition, weight and age of the patient, etc.

Oligopeptides according to the invention, such as, for example, acetate salts or esters of SEQ ID NO:2 and/or SEQ ID NO:3, are generally used in pharmaceutical compositions containing the active ingredient with a carrier, vehicle, diluent and/or excipient in an amount of about 0.1 to 99 wt % and preferably about 25-85 wt %. Pharmaceutical compositions may be formulated using carriers, diluents and/or excipients known in the art, for example, see *Remington's Pharmaceutical Sciences*, Remington, J. P., Easton, Pa.: Mack Pub. Co., 1990. The compounds may be administered in any desired form, including, for example, parenterally, orally, injection, transdermally or by suppository using known methods. intraperitoneal delivery is a preferred means of administration.

The active molecule may be administered directly in a suitable vehicle, such as, for example, phosphate-buffered saline ("PBS") or solutions in alcohol or DMSO. Pursuant to preferred embodiments of the invention, however, the active molecule is administered through a single dose delivery using a drug-delivery system. A suitable drug-delivery system would be pharmacologically inactive or at least tolerable. It should preferably not be immunogenic nor cause inflammatory reactions, and should permit release of the active molecule so as to maintain effective levels thereof over the desired time period. Alternatives are known in the art as suitable for purposes of sustained release and are contemplated as within the scope of the invention. Suitable delivery vehicles include, but are not limited to, the following: microcapsules or microspheres; liposomes and other lipid-based release systems; viscous installates; absorbable and/or biodegradable mechanical barriers and implants; and polymeric delivery materials, such as polyethylene oxide/polypropylene oxide block copolymers, polyesters, cross-linked polyvinyl alcohols, polyanhydrides, polymethacrylate and polymethacrylamide hydrogels, anionic carbohydrate polymers, etc. Useful delivery systems are well known in the art.

One formulation to achieve the active molecule release comprises injectable microcapsules or microspheres made from a biodegradable polymer, such as poly(dl-lactide), poly (dl-lactide-co-glycolide), polycaprolactone, polyglycolide, polylactic acid-co-glycolide, poly(hydroxybutyric acid), polyesters or polyacetals. Injectable systems comprising microcapsules or microspheres having a diameter of about 50 to about 500 micrometers offer advantages over other delivery systems. For example, they generally use less active molecules and may be administered by paramedical personnel. Moreover, such systems are inherently flexible in the design of the duration and rate of separate drug release by selection of microcapsule or microsphere size, drug loading and dosage administered. Further, they can be successfully sterilized by gamma irradiation.

The design, preparation, and use of microcapsules and microspheres are well within the reach of persons skilled in the art and detailed information concerning these points is available in the literature. Biodegradable polymers (such as lactide, glycolide and caprolactone polymers) may also be used in formulations other than microcapsules and microspheres; e.g., pre-made films and spray-on films of these polymers containing the active molecule would be suitable for use in accordance with the invention. Fibers or filaments comprising the active molecule are also contemplated as within the scope of the invention.

Another highly suitable formulation for a single-dose delivery of the active molecule in accordance with the invention involves liposomes. The encapsulation of an active molecule in liposomes or multilamellar vesicles is a well-known technique for targeted drug delivery and prolonged drug residence. The preparation and use of drug-loaded liposomes is well within the reach of persons skilled in the art and well documented in the literature.

Yet another suitable approach for single-dose delivery of an active molecule in accordance with the invention involves the use of viscous installates. In this technique, high molecular weight carriers are used in admixture with the active molecule, giving rise to a structure that produces a solution with high viscosity. Suitable high molecular weight carriers include, but are not limited to, the following: dextrans and cyclodextrans; hydrogels; (cross-linked) viscous materials, including (cross-linked) viscoelastics; carboxymethylcellulose; hyaluronic acid; and chondroitin sulfate. The preparation and use of drug-loaded viscous installates is well known to persons skilled in the art.

Pursuant to yet another approach, the active molecule may be administered in combination with absorbable mechanical barriers such as oxidized regenerated cellulose. The active molecule may be covalently or non-covalently (e.g., jonically) bound to such a barrier, or it may simply be dispersed therein.

Either fluid or solid unit dosage forms can be readily prepared for oral administration. For example, acetate salts or esters of SEQ ID NO:2 and/or SEQ ID NO:3 can be admixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used where appropriate or desirable. Capsules may be formulated by mixing, for example, acetate salts or esters of SEQ ID NO:2 and/or SEQ ID NO:3, with an inert pharmaceutical diluent and inserting this mixture into a hard gelatin capsule having the appropriate size. If soft capsules are desired, then a slurry of the compound with an acceptable vegetable, light petroleum or other inert oil can be encapsulated in a gelatin capsule or similar capsules.

Suspensions, syrups and elixirs may be used for oral administration of fluid unit dosage forms. A fluid preparation including oil may be used for oil soluble forms. A vegetable oil such as corn oil, peanut oil or sunflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener (such as sugar, saccharin, or a biological sweetener, preferably a low carbohydrate sweetener, such as manitol or sorbitol) and a flavoring agent in the form of an elixir.

Pharmaceutical compositions for parenteral and suppository administration can also be obtained using techniques standard in the art. In an exemplary embodiment, acetate salt or ester of SEQ ID NO:2 and/or SEQ ID NO:3 is administered as a pharmaceutical agent suitable for oral administration. In another exemplary embodiment, acetate salts or esters of SEQ ID NO:2 and/or SEQ ID NO:3 may be injected using an appropriate vehicle such as saline.

The pharmaceutical carriers acceptable for the purposes of this invention include carriers that do not adversely affect the drug, the host, or the material comprising the drug delivery device. Suitable pharmaceutical carriers include sterile water, saline, dextrose, dextrose in water or saline condensation products of castor oil and ethylene oxide (combining about 30 to 35 moles of ethylene oxide per mole of castor oil), liquid acid, lower alkanols, oils such as corn oil, peanut oil, sesame oil and the like, with emulsifiers such as mono- or diglyceride of a fatty acid; or a phosphatide, e.g., lecithin, and the like; glycols, polyalkylene glycols, aqueous media in the presence of a suspending agent, for example, sodium carboxymethyl cellulose, sodium alginate, poly(vinylpyrrolidone), and the like, alone, or with suitable dispensing agents such as lecithin, polyoxyethylene stearate, and the like. The carrier may also contain adjuvants such as preserving agents, stabilizing agents, wetting agents, emulsifying agents and the like together with penetration enhancers and an oligopeptide of the invention such as acetate salts or esters of SEQ ID NO:2 and/or SEQ ID NO:3.

The effective dose for mammals may vary due to such factors as age, body mass, activity level or condition of the subject being treated. For example, an effective dosage of acetate salts or esters of SEQ ID NO:2 and/or SEQ ID NO:3 is from about 0.1 to about 35 milligrams per kilogram when administered parenterally. Dosages may be significantly higher for administration in oral or other external form.

In an exemplary embodiment, the method includes administering an effective amount of an oligopeptide of the invention, such as acetate salts or esters of SEQ ID NO:2 and/or SEQ ID NO:3, or an effective amount of a pharmaceutical composition containing an oligopeptide of the invention, such as acetate salts or esters of SEQ ID NO:2 and/or SEQ ID NO:3, to a subject, such as a mammal (e.g., a human), thought to be in need of such treatment. For example, a subject that may benefit from the method is a subject believed to be suffering from an acute inflammation disorder such as sepsis or septic shock.

The invention is further explained with the aid of the following illustrative examples.

EXAMPLES

Peptide Synthesis

Peptides mentioned here were prepared commercially by solid-phase synthesis using the fluorenylmethoxycarbonyl (Fmoc)/tert-butyl-based methodology with 2-chlorotrityl chloride resin as the solid support. The side-chain of glutamine was protected with a trityl function. The peptides were synthesized manually. Each coupling consisted of the following steps: (i) removal of the alpha-amino Fmoc-protection by piperidine in dimethylformamide (DMF), (ii) coupling of the Fmoc amino acid (3 eq) with diisopropylcarbodiimide (DIC)/1-hydroxybenzotriazole (HOBt) in DMF/N-methylformamide (NMP) and (iii) capping of the remaining amino functions with acetic anhydride/diisopropylethylamine (DIEA) in DMF/NMP. Upon completion of the synthesis, the peptide resin was treated with a mixture of trifluoroacetic acid (TFA)/$H_2O$/triisopropylsilane (TIS) 95:2.5:2.5. After 30 minutes TIS was added until decolorization. The solution was evaporated in vacuo and the peptide precipitated with diethyl ether. The crude peptides were dissolved in water (50-100 mg/ml) and purified by reverse-phase high-performance liquid chromatography (RP-HPLC). HPLC conditions were: column: Vydac TP21810C18 (10×250 mm); elution system: gradient system of 0.1% TFA in water v/v (A) and 0.1% TFA in acetonitrile (ACN) v/v (B); flow rate 6 ml/min; absorbance was detected from 190-370 nm. There were different gradient systems used. For example for peptides LQG and LQGV (SEQ ID NO:3): 10 minutes 100% A followed by linear gradient 0-10% B in 50 minutes. For example for peptides VLPALP (SEQ ID NO:6) and VLPALPQ (SEQ ID NO:5): 5 minutes 5% B followed by linear gradient 1% B/minute. The collected fractions were concentrated to about 5 ml by rotation film evaporation under reduced pressure at 40° C. The remaining TFA was exchanged against acetate by eluting two times over a column with anion exchange resin (Merck II) in acetate form. The elute was concentrated and lyophilized in 28 hours. Peptides later were prepared for use by dissolving them in PBS.

NO Experiment

Cell culture. The RAW 264.7 murine macrophage cell line, obtained from American Type Culture Collection (Manassas, Va., USA), were cultured at 37° C. in 5% $CO_2$ using DMEM containing 10% fetal calf serum (FCS), 50 U/ml penicillin, 50 μg/ml streptomycin, 0.2 M Na-pyruvate, 2 mM glutamine and 50 μM 2-mercaptoethanol (Bio Whittaker, Europe). The medium was changed every 2 days.

Nitrite measurements. Nitrite production was measured in the RAW 264.7 macrophage supernatants. The cells (7.5×$10^5$/ml) were cultured in 48-well plates in 500 ml of culture medium. The cells were stimulated with LPS (10 microg/ml) and/or peptide (1 pg/ml, 1 ng/ml, 1 μg/ml) for 24 hours, then the culture media were collected. Nitrite was measured by adding 100 microl of Griess reagent (Sigma) to 100 microl samples of culture medium. The $OD_{540}$ was measured using a microplate reader, and the nitrite concentration was calculated by comparison with the $OD_{540}$ produced using standard solutions of sodium nitrite in the culture medium.

Results NO Experiment

NO production is a central mediator of the vascular and inflammatory response. Our results show that macrophages (RAW 264.7) stimulated with LPS produce large amount of NO. However, those cells co-stimulated with SEQ ID NO:3 or SEQ ID NO:2 even in a very low dose (1 pg/ml) inhibited the production of NO.

Example I

SEQ ID NO:2 was tested and compared with PBS (control) in a double blind animal study for the peptide's relative ability to aid recovery in a mouse renal ischemia reperfusion test. In this test, the mice were anesthetized, and one kidney from each mouse was removed. The other kidney was tied off for 25 minutes, and the serum urea levels were allowed to increase. Both before and after tying off, the peptide was administered to thirty (30) different mice (5 mg oligopeptide/kg body mass intravenously), after which, the mortality of the mice was determined for each oligopeptide as well as was the BUN concentration at two hours, 24 hours and 72 hours. The results are shown in Table 1 below.

Under inhalation anesthesia, the left kidney with its artery and vein was isolated and occluded for 25 minutes using a microvascular clamp. During surgery animals were placed on a heating path to maintain body temperature at 37° C. Five minutes before placing the clamp, and 5 minutes before releasing the clamp, 5 mg/kg of peptide, dissolved in 0.1 mL of sterile saline, was administered intravenously. After reperfusion of the left kidney the right kidney was removed. Kidney function was assessed by measuring blood urea nitrogen before clamping, and at 2, 24, and 72 hours after reperfusion.

| Results - Table 1 (mortality at 72 hours post-reperfusion). | |
| --- | --- |
| PBS | (AQGV) (SEQ ID NO: 2) |
| 6/10 | 0/10 |
| *P < (vs PBS) | 0.01 |

*2 × 2 Chi-square test. df = 1

As can be seen, mice administered the oligopeptide AQGV (SEQ ID NO:2) did much better in terms of both survival (a significant reduction in mortality versus the PBS control group) and reduced BUN concentration than the control group.

Example II

SEQ ID NO:3 was tested for its capacity to reduce BUN levels in the mice test as described above. The results are shown in Table 2.

TABLE 2

BUN after 25 mm renal ischemia tested in mice with peptides A-J

| Peptide | | t = 0 hr | 2 hr | 24 hr | 72 hr | N-term: | C-term: CARBOXYL FREE |
| --- | --- | --- | --- | --- | --- | --- | --- |
| AQGV (SEQ ID NO: 2) | Mean | 9.713333 | 16.62 | 26.36 | 22.31 | NMPF-46 | AQGV (SEQ ID NO: 2) |
| | Sd | 1.882722 | 2.185203 | 20.62105 | 15.96444 | | |
| | N | 30 | 10 | 20 | 10 | | |
| LQGV (SEQ ID NO: 3) | mean | 7.518182 | 17.53333 | 56.08333 | 73.17778 | NMPF-4 | LQGV (SEQ ID NO: 3) |
| | SD | 1.537356 | 2.956913 | 14.53573 | 23.3083 | | |
| | N | 22 | 3 | 18 | 9 | | |
| PBS control | mean | 8.172414 | 15.0875 | 56.81 | 82.075 | | |
| | SD | 1.549169 | 2.215167 | 22.4659 | 34.82713 | | |
| | N | 29 | 8 | 15 | 4 | | |

At 24 hour post-reperfusion statistical analyses revealed P-values of:

p = 0.0008 NMPF-46 AQGV    (SEQ ID NO: 2)

p = 0.9301 NMPF-4  LQGV    (SEQ ID NO: 3)

At 24 hour post-reperfusion statistical analyses revealed P-values of:

p < 0.0001 NMPF-46 AQGV    (SEQ ID NO: 2)

p = 0.8328 NMPF-4  LQGV    (SEQ ID NO: 3)

P values were calculated by Mann Whitney U-test (SPSS for Windows).

Example III

To determine dose-response relationships SEQ ID NO:2, was tested in a dose-response manner in the mice test as described above. Peptides were tested at 0.3, 1, 3, 10 and 30 mg/kg dosages given as described in Example I. Serum urea levels are presented in Table 3. Statistical significance of changes in serum urea levels is presented in Table 4. Mortality data is presented in Table 5.

TABLE 3

Urea Levels in dose-response experiment

|  | 24 h | 72 h |
|---|---|---|
| PBS | 57.8 | 85.4 |
| Peptide D (AQG) 0.3 mg/kg | 38.4 | 30.4 |
| Peptide D (AQG) 1.0 mg/kg | 48.4 | 38.4 |
| Peptide D (AQG) 3.0 mg/kg | 39.3 | 40.3 |
| Peptide D (AQG) 10.0 mg/kg | 46.8 | 25.8 |
| Peptide D (AQG) 30.0 mg/kg | 52.8 | 58.9 |
| Peptide B (AQGV (SEQ ID NO: 2)) 0.3 mg/kg | 62.4 | 86.7 |
| Peptide B (AQGV (SEQ ID NO: 2)) 1.0 mg/kg | 50.0 | 52.6 |
| Peptide B (AQGV (SEQ ID NO: 2)) 3.0 mg/kg | 37.4 | 19.6 |
| Peptide B (AQGV (SEQ ID NO: 2)) 10.0 mg/kg | 41.2 | 37.1 |
| Peptide B (AQGV (SEQ ID NO: 2)) 30.0 mg/kg | 47.8 | 38.0 |

| standard error | 24 h | 72 h |
|---|---|---|
| PBS | 7.1 | 14.7 |
| Peptide D (AQG) 0.3 mg/kg | 8.6 | 3.5 |
| Peptide D (AQG) 1.0 mg/kg | 7.2 | 10.2 |
| Peptide D (AQG) 3.0 mg/kg | 3.5 | 10.7 |
| Peptide D (AQG) 10.0 mg/kg | 8.0 | 3.4 |
| Peptide D (AQG) 30.0 mg/kg | 9.5 | 12.9 |
| Peptide B (AQGV (SEQ ID NO: 2)) 0.3 mg/kg | 10.8 | 14.1 |
| Peptide B (AQGV (SEQ ID NO: 2)) 1.0 mg/kg | 11.7 | 14.3 |
| Peptide B (AQGV (SEQ ID NO: 2)) 3.0 mg/kg | 7.6 | 2.6 |
| Peptide B (AQGV (SEQ ID NO: 2)) 10.0 mg/kg | 8.5 | 6.9 |
| Peptide B (AQGV (SEQ ID NO: 2)) 30.0 mg/kg | 5.8 | 7.8 |

Figure 3A:
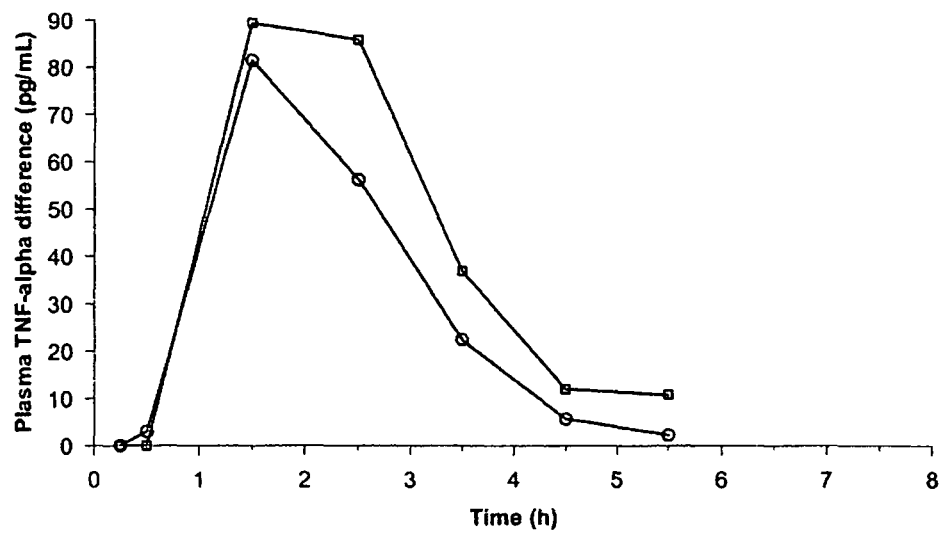
FIGS. 3A and 3B. are graphs depicting average changes in the concentration of TNF-α and CRP in the plasma of subjects respectively. All subjects were treated with 4 ng/kg LPS 30 minutes prior to administration of a placebo (squares) or 10 mg/kg EA-230 (circles).
Figure 3B:
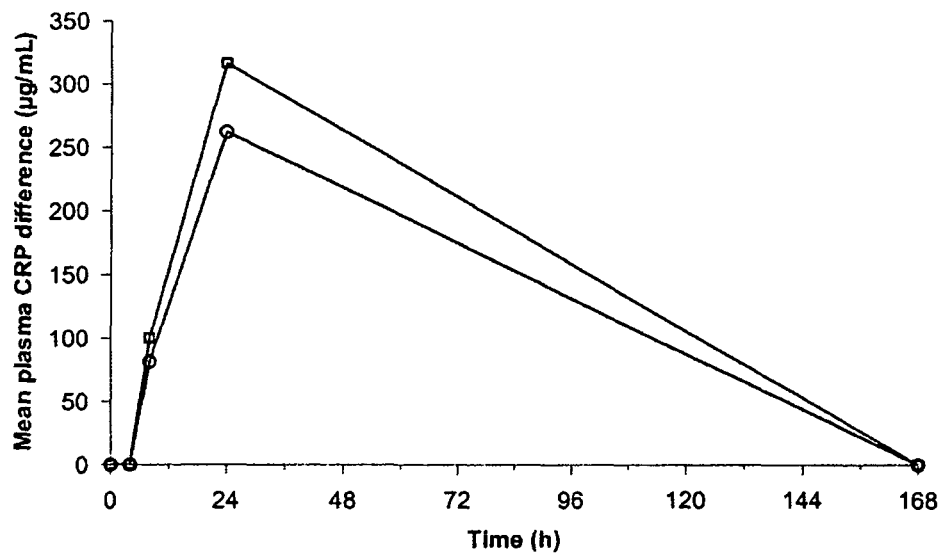

TABLE 4 statistical significance /p values (Mann Whitney U-Test) of serum urea levels in dose-response experiment 72 hours post-clamping. PBS control compared to peptide administered groups. (See, FIG. 3).

|  | 72 h |
|---|---|
| PBS | NA |
| AQG 0.3 mg/kg | 0.001 |
| AQG 1.0 mg/kg | 0.009 |
| AQG 3.0 mg/kg | 0.02 |
| AQG 10.0 mg/kg | 0.000 |
| AQG 30.0 mg/kg | 0.23 |
| AQGV (SEQ ID NO: 2) 0.3 mg/kg | 0.88 |
| AQGV (SEQ ID NO: 2) 1.0 mg/kg | 0.054 |
| AQGV (SEQ ID NO: 2) 3.0 mg/kg | 0.000 |
| AQGV (SEQ ID NO: 2) 10.0 mg/kg | 0.001 |
| AQGV (SEQ ID NO: 2) 30.0 mg/kg | 0.003 |

TABLE 5

Mortality in dose-response experiment

|  | 24 h | 72 h |
|---|---|---|
| PBS | 0-9 | 4-8 |
| AQGV (SEQ ID NO: 2) 0.3 mg/kg | 0-9 | 2-10 |
| AQGV (SEQ ID NO: 2) 1.0 mg/kg | 0-10 | 1-8 |
| AQGV (SEQ ID NO: 2) 3.0 mg/kg | 1-10 | 0-10 |
| AQGV (SEQ ID NO: 2) 10.0 mg/kg | 0-10 | 0-8 |
| AQGV (SEQ ID NO: 2) 30.0 mg/kg | 0-8 | 3-10 |

Example IV

Septic shock experiments were set up to determine which peptide was best suited to battle acute inflammation.

Mice used in sepsis or septic shock experiments: Female BALB/c mice of 8-12 weeks of age were used for all experiments. The animals were bred in our facility under specific pathogen-free conditions according to the protocols described in the Report of European Laboratory Animal Science Associations (FELASA) Working group on Animal Health (Laboratory Animals 28: 1-24, 1994).

Injection protocols: For the endotoxin model, BALB/c mice were injected i.p. with 150-300 µg LPS (*E. coli* 026:B6; Difco Lab., Detroit, Mich., USA). Control groups were treated with PBS i.p. only. To test the effect of peptides, they were dissolved in PBS and injected i.p. at predetermined points in time after LPS treatment.

Mice were scored for sickness severity using the following measurement scheme:

0 No abnormalities.
1 Percolated fur, but no detectable behavior differences compared to normal mice.
2 Percolated fur, huddle reflex, responds to stimuli (such as tap on cage), just as active during handling as healthy mouse.
3 Slower response to tap on cage, passive or docile when handled, but still curious when alone in a new setting.
4 Lack of curiosity, little or no response to stimuli, quite immobile.
5 Labored breathing, inability or slow to self-right after being rolled onto back (moribund, sacrificed).
D Dead A first set of septic shock experiments were set up to determine if the peptide SEQ ID NO:3 was capable of inhibiting LPS-induced septic shock in mice by treating mice with a single dose of peptide at 2 hours after LPS treatment. Peptides were used at 5 mg/kg bodyweight. ALB/c mice were injected i.p. with escalating doses LPS (*E. coli* 026:B6; Difco Lab., Detroit, Mich., USA), predetermined to be leading to 80-100% mortality in 24 72 hours. Control groups were treated with PBS i.p. only and showed no mortality. Results are presented in Table 6.

A second set of septic shock experiments were set up to determine if the peptides SEQ ID NO:3 and SEQ ID NO:2 were able to inhibit high dose LPS-induced septic shock in mice by treating mice with a double dose of peptide at 2 and 24 hours after LPS treatment. At each treatment, peptides were used at 5 mg/kg bodyweight. BALB/c mice were injected i.p. with high doses LPS (*E. coli* 026:B6; Difco Lab., Detroit, Mich., USA), predetermined to be leading to 80-100% mortality in 24-72 hours. Control groups were treated with PBS i.p. only and showed no mortality. Results are presented in Table 7.

A further set of septic shock experiments were set up to determine if the peptides SEQ ID NO:3 and SEQ ID NO:2 were most suited to be used early and/or late after or throughout the development of shock. For determining the percent of endotoxin shock survival after late or early treatment with peptide, BALB/c mice were injected i.p. with 300 µg LPS (*E. coli* 026:B6; Difco Lab.), predetermined to be leading to 100% mortality in 48 hours without peptide treatment. Control groups were treated with PBS i.p. only and showed no mortality. Results are presented in Table 8.

A comparative trial was set up to compare peptide MTR and SEQ ID NO:2. The comparative trial comprised 6 groups of 6 animals; two groups (1A and 1B) receiving placebo (PBS), one group (2) peptide MTR (source Pepscan, Lelystad, NL), one group (3) receiving peptide MTR (source Ansynth), one group (4) receiving peptide SEQ ID NO:2 (source Pepscan) and one group peptide SEQ ID NO:2 (source Ansynth). Peptide/placebo in these groups was administered 2 hours after LPS. LPS (source) was used at 10-11 mg/kg. Sickness scores were done at 0, 2, 22 26 42 and 48 hours after LPS injection. Results are presented in Table 9. Results To test the effect of peptide early in the development of shock, mice were treated at 2 hours or at 24 after treatment with varying doses of LPS by i.p. injection with test peptide at 5 mg/kg bodyweight. All LPS doses resulted in 100% mortality at 48-72 hours in the non-peptide treated mice. The results are shown in Table 6. SEQ ID NO:3 showed a marked protective effect against LPS-induced sepsis.

To evaluate the effect of peptide treatment at an early or late point in time of development of shock, mice were treated at 2 hours or at 24 after LPS injection by i.p. injection with test peptide at 5 mg/kg bodyweight. The mice were followed for 84 hours instead of for 48 hours in the earlier experiments. Table 8 depicts the results. SEQ ID NO:2 showed 100% survival and no remaining clinical signs of shock at 84 hours after LPS-treatment when given both early or late in the development of shock.

TABLE 8

Percent of mice surviving LPS-induced sepsis after treatment with a single injection of test peptide (at 5 mg/kg body weight) at 2 or 24 hours after induction of sepsis by treatment with LPS.

| | % SURVIVAL IN TIME (HOURS) | | | | |
|---|---|---|---|---|---|
| | 0 | 14 | 24 | 48 | 84 |
| TREATMENT 2 HOURS AFTER LPS TREATMENT | | | | | |
| PBS | 100 | 100 | 100 | 0 | 0 |
| LQGV (SEQ ID NO: 3) | 100 | 100 | 100 | 100 | 100 |
| AQGV (SEQ ID NO: 2) | 100 | 100 | 100 | 100 | 100 |
| TREATMENT 24 HOURS AFTER LPS TREATMENT | | | | | |
| PBS | 100 | 100 | 100 | 0 | 0 |
| LQGV SEQ ID NO: 3 | 100 | 100 | 100 | 0 | 0 |

TABLE 6

| | | | single dose administration 5 mg/kg | | | | | | | | | | | | |
|---|---|---|---|---|---|---|---|---|---|---|---|---|---|---|---|
| Peptide tested | LPS dose | n | effect at t = 24 hr | | | | | | | effect at t = 48 hr | | | | | |
| | | | 0 | 1 | 2 | 3 | 4 | 5 | D | 0 | 1 | 2 | 3 | 4 | 5 | D |
| LQGV (SEQ ID NO: 3) | 7* | 6 | | | 2 | 4 | | | | 6 | | | | | | |
| | 7** | 6 | 6 | | | | | | | 6 | | | | | | |
| | 8 | 6 | | | 5 | 1 | | | | | | 5 | 1 | | | |
| | 8 | 6 | | 3 | 3 | | | | | | | 4 | 2 | | | |
| | 10 | 6 | 6 | | | | | | | 6 | | | | | | |
| | 10 | 6 | | 2 | 2 | 1 | 1 | | | | 4 | 1 | | | | 1 |

TABLE 7

Peptide administered twice (t = 2 hr and t = 24 hr) 5 mg/kg at high LPS dose

| P | LPS dose | n | effect at t = 24 hr | | | | | | | effect at t = 48 hr | | | | | |
|---|---|---|---|---|---|---|---|---|---|---|---|---|---|---|---|
| | | | 0 | 1 | 2 | 3 | 4 | 5 | D | 0 | 1 | 2 | 3 | 4 | 5 | D |
| LQGV (SEQ ID NO: 3) | 10.5 | 5 | | | | | | 5 | | | | | | | 5 | |
| | 11 | 6 | | | | 2 | 4 | | | | | | 2 | 4 | | |
| AQGV (SEQ ID NO: 2) | 10.5 | 6 | | | 2 | 3 | | | | 5 | | | | | | |
| | 11 | 4 | | | 2 | 4 | | | | 6 | | | | | | |

TABLE 8-continued

Percent of mice surviving LPS-induced sepsis after treatment with a single injection of test peptide (at 5 mg/kg body weight) at 2 or 24 hours after induction of sepsis by treatment with LPS.

| | % SURVIVAL IN TIME (HOURS) | | | | |
|---|---|---|---|---|---|
| | 0 | 14 | 24 | 48 | 84 |
| AQGV SEQ ID NO: 2 | 100 | 100 | 100 | 100 | 100 |

TABLE 9 comparative trial MTR and AQGV, each from two sources

| | | Sickness scores | | | | | | |
|---|---|---|---|---|---|---|---|---|
| | No. | 0 hrs | 2 hrs | 22 hrs | 26 hrs | 42 hrs | 48 hrs | Survival % |
| Group 1A PBS | 1 | 0 | 2 | 4 | 4 | 5 | dead | |
| | 2 | 0 | 2 | 3 | 3 | 5 | dead | |
| | 3 | 0 | 2 | 5 | dead | | | |
| | 4 | 0 | 2 | 3 | 3 | 3 | 2 | |
| | 5 | 0 | 2 | 4 | 4 | dead | | |
| | 6 | 0 | 2 | 5 | 5 | dead | | |
| Group 1B PBS | 1 | 0 | 2 | 4 | 4 | 4 | dead | |
| | 2 | 0 | 2 | 5 | dead | | | |
| | 3 | 0 | 2 | 3 | 3 | 2 | 1 | |
| | 4 | 0 | 2 | 4 | dead | | | |
| | 5 | 0 | 2 | 4 | 4 | 5 | dead | |
| | 6 | 0 | 2 | 5 | 5 | dead | | 17% |
| Group 2 #970 MTR | 1 | 0 | 2 | dead | | | | |
| | 2 | 0 | 2 | 3 | 3 | 5 | dead | |
| | 3 | 0 | 2 | 2 | 2 | 2 | 2 | |
| | 4 | 0 | 2 | 2 | 2 | 2 | 2 | |
| | 5 | 0 | 2 | 2 | 2 | 4 | dead | |
| | 6 | 0 | 2 | 4 | 5 | dead | | 33% |
| Group 3 #Ansynth 12 MTR | 1 | 0 | 2 | 2 | 1 | 1 | 1 | |
| | 2 | 0 | 2 | 2 | 2 | 2 | 1 | |
| | 3 | 0 | 2 | 4 | 5 | dead | | |
| | 4 | 0 | 2 | 3 | 4 | 4 | dead | |
| | 5 | 0 | 2 | 2 | 2 | 3 | 5 | dead |
| | 6 | 0 | 2 | 2 | 2 | 2 | 2 | 50% |
| Group 4 #971 AQGV (SEQ ID NO:2) | 1 | 0 | 2 | 2 | 2 | 2 | 2 | |
| | 2 | 0 | 2 | 2 | 3 | 3 | 2 | 1 |
| | 3 | 0 | 2 | 2 | 2 | 2 | 2 | |
| | 4 | 0 | 2 | 2 | 2 | 2 | 2 | |
| | 5 | 0 | 2 | 2 | 4 | 5 | dead | |
| | 6 | 0 | 2 | 2 | 3 | 2 | 1 | 83% |
| Group 5 #Ansynth 46 AQGV (SEQ ID NO:2) | 1 | 0 | 2 | 3 | 3 | 2 | 1 | |
| | 2 | 0 | 2 | 3 | 3 | 3 | 1 | |
| | 3 | 0 | 2 | 2 | 2 | 2 | 1 | 1 |
| | 4 | 0 | 2 | 4 | 4 | 5 | dead | |
| | 5 | 0 | 2 | 2 | 2 | 1 | 1 | |
| | 6 | 0 | 2 | 2 | 2 | 1 | 1 | 83% |

LPS = 10-11 mg/kg
970 = 5 mg/kg
971 = 5 mg/kg
Ansynth 12 LPS treatment
Ansynth 46 compound treatment Example V Human Phase Trials Materials SEQ ID NO:2) was Used in Human Trials Identified as EA-230

The active compound (H-Ala-Gln-Gly-Val-OH.xAcOH) was manufactured by Diosynth, Oss, NL, whereas filling and finishing of the final product was performed by Octoplus, Leiden, NL. The injection fluid was supplied in 20 mL vials containing 11 mL of 40 mg/mL EA-230. The final product was a clear to slightly opalescent injection fluid. Batch No 05C21701-01A. An analyses report of the producer is included as Appendix 1.

Phosphate buffered saline (PBS) was used as placebo.
Lipopolysaccharide (LPS) was used in human trials
LPS is a USP reference standard derived from E. coli (EC6, Catalog No. 1235503), and was obtained from the following supplier:

U.S. Pharmacopoeia
12601 Twinbrook Parkway
Rockville, Md. 20852 (USA)
LPS was supplied in vials containing 1000 ng from a single batch.

Methodology:

The study consisted of two parts:

Part 1: A Phase I, double blind, randomized, single dose, placebo controlled, dose escalation study with 4 groups of 8 subjects (Groups 1-4). In each group 6 subjects were randomized to active medication and 2 to placebo. The first group received a single intravenous injection of EA-230 or placebo. After all subjects had completed Day 7 assessments, the safety review board decided on continuation of the study until the maximum tolerated dose had been assessed or the highest dose. Placebo subjects were pooled for analysis.

Part 2: A Phase I, double blind, randomized, single dose, placebo controlled study. The second part consisted of 1 group of 12 subjects (Group 5). All twelve subjects received LPS (4 ng/kg E. coli EC6) as a 2-minute injection, 30 minutes prior to EA-230 administration. Eight subjects received 10 mg/kg EA-230 (the most effective dose, as established by a biological assay (whole blood cell proliferation) during Part 1 of the study), and 4 subjects received placebo. Cytokines profiles were assessed to establish the effect of EA-230 on inflammatory parameters.

Number of Subjects:

44 planned, 44 randomized, 44 treated, 44 completed.
32 (4 groups of 8) in the first part and 12 (1 group) in the second part of the study.

Diagnosis and Main Criteria for Inclusion:

Healthy Caucasian male subjects, aged 18-50 years inclusive, with a BMI within 18-29 kg/m$^2$ inclusive.

Test Product, Dose and Mode of Administration, Batch Number:

Group 1: EA-230 1 mg/kg body weight, intravenous 2-min infusion, batch No 05C21701-01A.

Group 2: EA-230 3 mg/kg body weight, intravenous 2-min infusion, batch No 05C21701-01A.

Group 3: EA-230 10 mg/kg body weight, intravenous 15-min infusion, batch No 05C21701-01A.

Group 4: EA-230 30 mg/kg body weight, intravenous 15-min infusion, batch No 05C21701-01A.

Group 5: LPS, followed by EA-230 10 mg/kg, intravenous 15-min infusion, batch No 05C21701-01A Duration of Treatment:

Per subject, an hospitalization from the evening before administration until 24 hours post-dose and a follow up visit 7 days after hospitalization. The screening visit occurred within 21 days before study drug administration.

Reference therapy, dose and mode of administration:

Placebo: Phosphate buffered saline (PBS)
Group 1 to 4: PBS, intravenous 2- or 15-min infusion.

Group 5: LPS, followed by PBS, intravenous 15-min infusion.

Criteria for Evaluation:

Pharmacokinetics (part 1 and part 2):

AUC, clearance, volume of distribution and elimination half-life.

Safety (part 1 and part 2):

Adverse events (AEs), vital signs, ECG, hematology, clinical chemistry, and urinalysis.

Whole blood cell proliferation (part 1 and part 2)

Pharmacodynamics (part 2):

Measurement of body temperature, vital signs, and the following cytokines: TNFα, IL-6, IL-8, IL-10, CRP and granulocyte response following stimulation with LPS. Additional cytokines may be measured after completion of the present study on stored plasma samples.

Statistical Methods:

Pharmacokinetics (Part 1 and Part 2):

Plasma concentration time profiles of EA-230 were analyzed. Pharmacokinetic parameters AUC, clearance, volume of distribution and elimination half-life were obtained for EA-230.

Safety (Part 1 and Part 2):

Incidence of treatment emergent AEs and treatment emergent treatment related AEs were summarized. Hematological, biochemical, urinalysis parameters, vital signs and their changes from baseline were summarized over time using n, mean, standard deviation, median and range.

Results

Summary of Results:

Pharmacokinetics:

PK samples were collected pre-dose and from 5 minutes to 4 hours after the start of study drug administration.

Mean EA-230 concentration in plasma is depicted in FIG. 1.

Inter-subject variability in EA-230 concentration in plasma and derived PK parameters was high. The drug was rapidly eliminated: average concentrations were below LOQ by 15 minutes after the 1-mg/kg dose to 2 h after dosing after the 30-mg/kg dose. No first-order terminal elimination phase could be observed in the profiles. $C_{max}$ and $AUC_{last}$ values are summarized in the table below.

| Study part | Treatment | $C_{max}$ (µg/mL) | $AUC_{last}$ (µg · min/mL) |
|---|---|---|---|
| 1 | 1 mg/kg (N = 6) | 0.0325± | 0.150 ± 0.112 |
|   | 3 mg/kg (N = 6) | 0.132 ± 0.0764 | 0.706 ± 0.390 |
|   | 10 mg/kg (N = 6) | 1.60 ± 1.13 | 13.0 ± 9.11 |
|   | 30 mg/kg (N = 6) | 3.22 ± 1.08 | 35.7 ± 12.9 |
| 2 | LPS + 10 mg/kg | 1.71 ± 1.33 | 18.2 ± 15.7 |

Values are arithmetic means ± SD.

90% CIs of the mean $C_{max}$ and $AUC_{last}$ treatment ratios calculated using ANOVA model were wide, making estimates little reliable. Therefore, no conclusion on dose-linearity of EA-230 PK can be drawn.

Pharmacodynamics:

PD analysis was performed on data from Part 2 only. Samples for cytokines (IL-6, IL-8, IL-10, and TNF α) and granulocytes (WBC, basophils, eosinophils, lymphocytes, monocytes, and neutrophils) were taken up to 7.5 h after dosing. Samples for CRP measurement were taken up to 168 h after dosing.

Cytokines, WBC, neutrophils, and CRP showed an increase consecutive to LPS challenge. Other granulocytes differentials showed a decrease. Most cytokines and monocytes were back to baseline values by 7.5 h after dosing. Average concentration changes of IL-6, IL-8, TNF-α, and CRP were generally larger in the placebo subjects than in the active subjects, as depicted in FIGS. 2A, 2B, 3A, and 3B respectively.

Other PD variables profiles were similar in placebo and active subjects. No significant difference between placebo and active subjects in PD variables changes was observed at any time, except in 1 test out of the 84 performed.

Safety (Adverse Events):

Thirteen treatment-emergent AEs ("TEAEs") in 8 subjects occurred during the first part of the study and 28 in 12 subjects during the second part. All TEAEs were mild, except two moderate events in 1 placebo subject having been challenged with LPS. TEAEs deemed treatment-related by the investigator were few and included mostly mild nervous system disorders. No difference in AE occurrence was observed between placebo and active subjects. No increase in the number or intensity of AEs with the dose of EA-230 was observed during the escalating dose part. AEs occurred more frequently during Part 2 because of the LPS challenge. No SAE occurred during the study.

Twenty-four hours after study drug administration, 30 subjects (68%) presented at least 1 laboratory abnormality. The most frequently recorded laboratory abnormalities were a low total bilirubin level, a low cholesterol level, and a high protein level. Low total bilirubin level and low cholesterol level were more encountered in active than in placebo subjects. This difference was already observed at screening visit. None of the abnormalities were deemed clinically significant by the Investigator.

All 44 subjects had weak positive or positive level of urine urobilinogen 24 h after study drug administration. The same abnormality was already observed at screening visit for each subject. Five subjects had weak positive or positive level of occult blood in urine 24 h after treatment. Three subjects had urine pH value above normal range and two subjects had rare squamous epithelial cells in urine.

Twenty-four hours after study drug administration, 6 subjects (14%) presented vital signs abnormalities (3 low HR, 2 high DBP, and 1 low SBP). At follow-up, 5 subjects (1%) presented vital signs abnormalities (3 low SBP, 1 high DBP, and 1 high HR). These abnormal parameters were not considered clinically significant by the Investigator.

Subjects of Group 5 showed an increase of oral body temperature starting approximately 2 h after study drug administration and peaking around 4 h. Treatment with EA-230 seemed to significantly reduce the increase in body temperature (+0.6° C. in active subjects vs +1.6° C. in placebo subjects), 4.5 h after LPS challenge (p-value=0.018).

LPS challenge also caused a decrease in blood pressure which was less marked in active than in placebo subjects and an increase in HR.

No abnormality was observed in physical examinations performed 24 h after study drug administration and at follow-up.

No abnormal QTc was observed during the study. None of the occasional abnormal ECG parameters were considered clinically significant by the investigator.

EA 230 was rapidly eliminated from plasma. No conclusion on dose-linearity of EA 230 PK can be drawn because of large inter-subject variations in PK parameters.

Average concentration changes of IL-6, IL-8, TNF-α, and CRP were generally larger in the placebo subjects than in the active subjects after LPS challenge, but these differences were not significant.

Administration of a single dose of EA-230 was safe and well tolerated. No difference in AE number, abnormal laboratory parameters, vital signs, and ECG abnormalities were observed during the escalating dose part (from 1 mg/kg to 30 mg/kg).

The number of AEs, vital signs abnormalities and abnormal laboratory parameters were higher in Part 2 than in Part 1, because of the LPS challenge. EA-230 tended to reduce changes in blood pressure and body temperature in LPS-challenged subjects.

In conclusion, 44 healthy male subjects were included in the study, and all completed the study. The study was designed in two parts (Part 1 and Part 2).

Part 1 was a dose escalating study with 4 groups of 8 subjects (Group 1-4). In each group 6 subjects were randomized to active medication and 2 to placebo.

Group 1 received a single intravenous injection of EA-230 (1 mg/kg) or placebo.

Group 2 received a single intravenous injection of EA-230 (3 mg/kg) or placebo.

Group 3 received a single intravenous injection of EA-230 (10 mg/kg) or placebo.

Group 4 received a single intravenous injection of EA-230 (30 mg/kg) or placebo.

Part 2 consisted of 1 group of 12 subjects (Group 5) receiving LPS (4 ng/kg *E. coli* EC6) as a 2-minutes injection, 30 minutes prior to EA-230 administration. Eight subjects received EA-230 at the most effective dose (10 mg/kg), as established during Part 1, and 4 subjects received placebo.

Pharmacokinetics

PK samples were collected pre-dose and from 5 minutes to 4 h after the start of study drug administration.

Theoretically, $t_{max}$ should have been the end of infusion time. However, it was observed 5 minutes before the end of infusion in subjects treated with 10 mg/kg EA-230 alone and in 2 subjects treated with 30 mg/kg EA-230, and 10 minutes before the end of infusion in most subjects treated with 10 mg/kg EA-230 with LPS challenge. The investigator did not report any infusion problem for these subjects. Therefore, no obvious explanation can be provided for this peculiarity.

Inter-subject variability in EA-230 concentration in plasma and derived PK parameters was high. The drug was rapidly eliminated: average concentrations were below LOQ by 15 minutes after the 1-mg/kg dose to 2 h after dosing after the 30-mg/kg dose. No first-order terminal elimination phase could be observed in the profiles. 90% CIs of the mean $C_{max}$ and $AUC_{last}$ treatment ratios were wide, making estimates little reliable. Therefore, no conclusion on dose-linearity of EA-230 PK can be drawn.

Pharmacodynamics

PD analysis was performed on data from Part 2 only. Samples for cytokines (IL-6, IL-8, IL-10, and TNF-α) and granulocytes (WBC, basophils, eosinophils, lymphocytes, monocytes, and neutrophils) were taken up to 7.5 h after dosing. Samples for CRP measurement were taken up to 168 h after dosing.

Cytokines, WBC, neutrophils, and CRP showed an increase consecutive to LPS challenge. Other granulocytes differentials showed a decrease. Most cytokines and monocytes were back to baseline values by 7.5 h after dosing. Average concentration changes of IL-6, IL-8, TNF-α; and CRP were generally larger in the placebo subjects than in the active subjects. Other PD variables profiles were similar in placebo and active subjects. No significant difference between placebo and active subjects in PD variables changes was observed at any time, except in one test out of the 84 performed.

Safety

Thirteen treatment-emergent AEs (TEAEs) in 8 subjects occurred during the first part of the study and 28 in 12 subjects during the second part. All TEAEs were mild, except two moderate events in 1 placebo subject having been challenged with LPS. TEAEs deemed treatment-related by the investigator were scarce and included mostly mild nervous system disorders. No difference in AE occurrence was observed between placebo and active subjects. No increase in the number or intensity of AEs with the dose of EA-230 was observed during the escalating dose part. AEs occurred more frequently during Part 2 because of the LPS challenge. No SAE occurred during the study.

Twenty-four hours after study drug administration, 30 subjects (68%) presented at least 1 laboratory abnormality. The most frequently recorded laboratory abnormalities were a low total bilirubin level, a low cholesterol level, and a high protein level. Low total bilirubin level and low cholesterol level were more encountered in active than in placebo subjects. This difference was already observed at screening visit. None of the abnormalities were deemed clinically significant by the Investigator.

All 44 subjects had weak positive or positive level of urine urobilinogen 24 h after study drug administration. The same abnormality was already observed at screening visit for each subject. Five subjects had weak positive or positive level of occult blood in urine 24 h after treatment. Three subjects had urine pH value above normal range and two subjects had rare squamous epithelial cells in urine.

Twenty-four hours after study drug administration, 6 subjects (14%) presented vital signs abnormalities (3 low HR, 2 high DBP, and 1 low SBP). At follow-up, 5 subjects (11%) presented vital signs abnormalities (3 low SBP, 1 high DBP, and 1 high HR). These abnormal parameters were not considered clinically significant by the Investigator.

Subjects of Group 5 showed an increase of oral body temperature starting approximately 2 hours after study drug administration and peaking around 4 h. Treatment with EA-230 seemed to significantly reduce the increase in body temperature (+0.6° C. in active subjects vs +1.6° C. in placebo subjects), 4.5 h after LPS challenge (p-value=0.018).

LPS challenge also caused a decrease in blood pressure which was less marked in active than in placebo subjects and an increase in HR.

No abnormality was observed in physical examinations performed 24 h after study drug administration and at follow-up.

No abnormal QTc was observed during the study. None of the occasional abnormal ECG parameters were considered clinically significant by the Investigator.

In conclusion, administration of a single dose of EA-230 was safe and well tolerated. No difference in AE number, abnormal laboratory parameters, vital signs, and ECG abnormalities were observed between the different EA-230 doses (from 1 mg/kg to 30 mg/kg) during the escalating dose part.

The number of AEs, vital signs abnormalities and abnormal laboratory parameters were higher in Part 2 than in Part 1, due to the LPS challenge. EA-230 tended to reduce changes in blood pressure and body temperature in LPS-challenged subjects.

While this invention has been described in certain embodiments, the invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

REFERENCES

Khan N A, Khan A, Savelkoul H F, Benner R, Inhibition of septic shock in mice by an oligopeptide from the beta-chain of human chorionic gonadotropin hormone. Hum Immunol. 2002 January; 63(1):1-7

Benner R, Khan N A. Dissection of systems, cell populations and molecules. Scand J Immunol. 2005 July; 62 Suppl 1:62-6.

Cole L A, Kardana A, Park S-Y, Braunstein G D. The deactivation of hCG by nicking and dissociation. J Clin Endocr Metab 1993; 76:704-710

Alfthan H, Stenman U H. Pathophysiological importance of various molecular forms of human chorionic gonadotropin. Mol Cell Endocrinol 1996; 125:107-120

Kardana A, Elliott M M, Gawinowicz M A, Birken S, Cole L A. The heterogeneity of human chorionic gonadotropin (hCG). I. Characterization of peptide heterogeneity in 13 individual preparations of hCG. Endocrinology 1991; 129: 1541-1550

Cole L A, Kardana A, Andrade-Gordon P, Gawinowicz M A, Morris J C, Bergert E R, O'Connor J, Birken S. The heterogeneity of human chorionic gonadotropin (hCG). III. The occurrence and biological and immunological activities of nicked hCG. Endocrinology 1991; 129:1559-1567

Birken S, Maydelman Y, Gawinowicz M A. Preparation and analysis of the common urinary forms of human chorionic gonadotropin. Methods 2000; 21:3-14.

What is claimed is:

1. An acetate of the tetrapeptide, wherein the tetrapeptide is LQGV (SEQ ID NO: 3).

2. The acetate of the tetrapeptide of claim 1, wherein the acetate is the acetate salt or the ester of the tetrapeptide.

3. A composition comprising the acetate of the tetrapeptide of claim 1 together with a pharmaceutically acceptable excipient.

4. A method of treating an acute inflammatory condition in a subject, said method comprising:
   administering the acetate of the tetrapeptide of claim 1 to a subject having an acute inflammatory condition in an amount efficacious to reduce the inflammation in the subject as may be determined by a decrease in serum IL-6 levels in the subject.

5. An acetate of the tetrapeptide, wherein the tetrapeptide is AQGV (SEQ ID NO: 2).

6. A method of reducing inflammation in a subject, said method comprising:
   administering the acetate of the tetrapeptide AQGV (SEQ ID NO: 2) to a subject having an acute inflammatory condition in an amount efficacious to reduce the inflammation in the subject as may be determined by a decrease in serum IL-6 levels in the subject.

* * * * *

UNITED STATES PATENT AND TRADEMARK OFFICE
CERTIFICATE OF CORRECTION

PATENT NO. : 8,680,059 B2
APPLICATION NO. : 11/600294
DATED : March 25, 2014
INVENTOR(S) : Nisar Ahmed Khan and Robbert Benner Page 1 of 1

It is certified that error appears in the above-identified patent and that said Letters Patent is hereby corrected as shown below:

On the title page:
In ITEM (63) Related U.S. Application Data
on the last line, change "Mar. 3," to --Mar. 29,--

Signed and Sealed this
Twenty-second Day of September, 2015

Michelle K. Lee
*Director of the United States Patent and Trademark Office*